(12) United States Patent
Vaughan

(10) Patent No.: US 8,821,546 B2
(45) Date of Patent: Sep. 2, 2014

(54) VERTEBRAL SCREW ARRANGEMENT WITH LOCKING PIN

(71) Applicant: Paul A. Vaughan, Dallas, TX (US)

(72) Inventor: Paul A. Vaughan, Dallas, TX (US)

(73) Assignee: Stanus Investments, Inc., Dallas, TX (US)

( * ) Notice: Subject to any disclaimer, the term of this patent is extended or adjusted under 35 U.S.C. 154(b) by 0 days.

(21) Appl. No.: 14/184,579

(22) Filed: Feb. 19, 2014

(65) Prior Publication Data
US 2014/0172025 A1 Jun. 19, 2014

Related U.S. Application Data

(63) Continuation-in-part of application No. 11/935,932, filed on Nov. 6, 2007, now abandoned.

(51) Int. Cl.
*A61B 17/70* (2006.01)
*A61B 17/86* (2006.01)

(52) U.S. Cl.
CPC ............. *A61B 17/8625* (2013.01); *A61B 17/70* (2013.01)
USPC ...................................................... 606/246

(58) Field of Classification Search
USPC ........... 606/70–71, 86 B, 280–281, 283–284, 606/902–906, 915, 246
See application file for complete search history.

(56) References Cited

U.S. PATENT DOCUMENTS

| 3,579,831 A | 5/1971 | Stevens et al. |
| 4,175,555 A | 11/1979 | Herbert |
| 4,463,753 A | 8/1984 | Gustilo |
| 4,611,581 A | 9/1986 | Steffee |
| 4,648,388 A | 3/1987 | Steffee |
| 4,655,199 A | 4/1987 | Steffee |
| 4,696,290 A | 9/1987 | Steffee |
| 4,719,905 A | 1/1988 | Steffee |
| 4,722,331 A | 2/1988 | Fox |
| 4,771,767 A | 9/1988 | Steffee |

(Continued)

FOREIGN PATENT DOCUMENTS

| WO | WO-03/028538 | 4/2003 |
| WO | WO-2005/096971 | 4/2005 |

OTHER PUBLICATIONS

Instrumentation Systems of Scoliosis Surgery, Internet website www.scoliosis.org/resources/medicalupdates/intrumentationsystems.php, National Scoliosis Foundation, Nov. 2, 2004, 2 pgs.

(Continued)

*Primary Examiner* — Sameh Boles
(74) *Attorney, Agent, or Firm* — Wilmer Cutler Pickering Hale and Dorr LLP

(57) ABSTRACT

Techniques for anterior partial transpedicular stabilization are disclosed. The techniques may be realized as a vertebral stabilization assembly including a first vertebral screw having a shaft with a first end, a threaded portion, and an engaging portion, and a second vertebral screw having a shaft with a first end, a threaded portion, and an engaging portion, the threaded portions configured for threading engagement of the vertebral screw with a vertebral body of a first vertebra. The vertebral stabilization assembly may further include a beveled connecting member having a first end and a second end configured to be disposed adjacent to a first side portion of an anterior side of the first vertebra, the first end of the beveled connecting member configured to engage with the first vertebral screw and the second vertebral screw.

17 Claims, 22 Drawing Sheets

(56) References Cited

U.S. PATENT DOCUMENTS

| | | |
|---|---|---|
| 4,854,311 A | 8/1989 | Steffee |
| 5,005,562 A | 4/1991 | Cotrel |
| 5,019,079 A | 5/1991 | Ross |
| 5,092,866 A | 3/1992 | Breard et al. |
| 5,180,381 A | 1/1993 | Aust et al. |
| 5,478,341 A | 12/1995 | Cook et al. |
| 5,486,176 A | 1/1996 | Hildebrand et al. |
| 5,496,322 A | 3/1996 | Mathews |
| 5,542,847 A | 8/1996 | Margulies |
| 5,569,248 A | 10/1996 | Mathews |
| 5,584,834 A | 12/1996 | Errico et al. |
| 5,603,713 A | 2/1997 | Aust et al. |
| 5,620,443 A | 4/1997 | Gertzbein et al. |
| 5,681,311 A | 10/1997 | Foley et al. |
| 5,683,391 A | 11/1997 | Boyd |
| 5,727,941 A | 3/1998 | Kesling |
| 5,728,097 A | 3/1998 | Mathews |
| 5,776,135 A | 7/1998 | Errico et al. |
| 5,814,046 A | 9/1998 | Hopf |
| 5,843,082 A | 12/1998 | Yuan et al. |
| 5,876,402 A | 3/1999 | Errico et al. |
| 5,904,683 A | 5/1999 | Pohndorf et al. |
| 5,947,967 A | 9/1999 | Barker |
| 5,976,135 A | 11/1999 | Sherman et al. |
| 6,001,101 A | 12/1999 | Augagneur et al. |
| 6,030,389 A | 2/2000 | Wagner et al. |
| 6,056,749 A | 5/2000 | Kuslich |
| 6,063,089 A | 5/2000 | Errico et al. |
| 6,066,140 A | 5/2000 | Gertzbein et al. |
| 6,083,224 A | 7/2000 | Gertzbein et al. |
| 6,106,527 A | 8/2000 | Wu et al. |
| 6,120,503 A | 9/2000 | Michelson |
| 6,132,434 A | 10/2000 | Sherman et al. |
| 6,135,001 A | 10/2000 | Miazga et al. |
| 6,136,002 A | 10/2000 | Shih et al. |
| 6,136,003 A | 10/2000 | Hoeck et al. |
| 6,139,551 A | 10/2000 | Michelson et al. |
| RE37,005 E | 12/2000 | Michelson et al. |
| 6,156,037 A | 12/2000 | LeHuec et al. |
| 6,167,145 A | 12/2000 | Foley et al. |
| 6,187,005 B1 | 2/2001 | Brace et al. |
| 6,190,388 B1 | 2/2001 | Michelson et al. |
| 6,193,721 B1 | 2/2001 | Michelson |
| RE37,161 E | 5/2001 | Michelson et al. |
| 6,228,085 B1 | 5/2001 | Theken et al. |
| 6,235,034 B1 | 5/2001 | Bray |
| 6,517,541 B1 | 2/2003 | Sesic |
| 6,533,787 B1 | 3/2003 | Lenke et al. |
| 6,620,195 B2 | 9/2003 | Goble et al. |
| 6,669,698 B1 | 12/2003 | Tromanhauser et al. |
| 6,761,721 B2 | 7/2004 | Burgess et al. |
| 6,899,714 B2 | 5/2005 | Vaughan |
| 7,087,056 B2 | 8/2006 | Vaughan |
| 7,780,710 B2 * | 8/2010 | Orbay et al. .......... 606/286 |
| 2003/0135216 A1 | 7/2003 | Sevrain |
| 2004/0193161 A1 | 9/2004 | Vaughan |
| 2005/0021040 A1 | 1/2005 | Bertagnoli |
| 2005/0085813 A1 | 4/2005 | Spitler et al. |
| 2005/0203522 A1 | 9/2005 | Vaughan |
| 2005/0240183 A1 | 10/2005 | Vaughan |
| 2005/0267473 A1 | 12/2005 | Vaughan |
| 2005/0288673 A1 | 12/2005 | Catbagan et al. |
| 2006/0149243 A1 | 7/2006 | Vaughan |
| 2006/0173459 A1 | 8/2006 | Kay et al. |

OTHER PUBLICATIONS

AcroMed Spinal Solutions for Thoracolumbar Trauma & Tumor, 1996, 10 pgs., AcroMed, Inc., Cleveland, OH.

Akbarnia PDR198 Instruments—Posterolateral Decompression & Reconstruction—Ordering Information, AcroMed Spine Tools. 1996, 2 pgs., AcroMed, Inc. Cleveland, OH.

C.V. Burton, "The present role of Titanium Cage fusion in Spine Cord," Internet website www.spineuniverse.com/surgery/procedures/cage2fusion.html, May 12, 1997, 3 pgs.

G.E. Rodts, Jr, MD, "What Should I know about lumbar fusion?," Dr Spine talks about exercise and back pain, Internet website www.spineuniverse.com/surgery/specialist/feature0130.html Mar. 28, 2001, 3 pages.

G.M. Amunddson, M.D., "Low Back Pain," Internet website www.spineuniverse.com/conditions/detail/lowback_amundson.html, Mar. 28, 2001, 4 pgs.

J.W. Brantigan, M.D., Lumbar I/F Cage® With VSP® Spinal System for PLIF, 1999, 16 pgs., DePuy/AcroMed, Inc., Cleveland, OH.

Kaneda SR (Smooth Rod)—Anterior Spinal System Titanium—Ordering Information for implants and instruments, 1996, 6 pgs., AcroMed, Inc., Cleveland, OH.

Laminectomy and Laminotomy—Low back Surgery to reduce your pain, 1997, 16 pags., Krames Communication, San Bruno CA.

Lumbar Disk Surgery—Treating Low Back Pain and Sciatica, 2000, 8 pgs., The StayWell Company, San Bruno, CA.

Lumbar Epidural Injections—Diagnosis and Treatment to help reduce pain, 1999, 8 pages, The StayWell Company, San Bruno, CA.

Lumbar Microsurgery—Low-back Surgery to reduce your pain, 1998, 16 pgs, The StayWell Company, San Bruno, CA.

M.R. Mclaughlin, M.D., "Image-guided Spinal Surgery," Internet website www.spineuniverse.com/technology/ak_mclaughlin_image-guided.html, Mar. 28, 2001, 2 pgs.

Spinal Fusion—Understanding your Surgency (pamphlet), 1999, 15 pgs., The StayWell Company, San Bruno, CA.

Spine Fusion Surgery—"Bone Growth Stimulators," Internet website www.orthofix.com/OFProd/ofsite/T1121c.htm, Mar. 28, 2001, 4 pgs.

Surgical technique for anterior thoracolumbar corpectomy, graft placement and stabilization using the Kaneda SR® Anterior Spinal System, 1996, 12 pgs., AcroMed, Inc., Cleveland, OH.

Surgical technique for anterior thoracolumbar corpectomy, graft placement and stabilization using the University$^{AM}$ Plate—Titanium Anterior System™, 1996, 8 pgs., AcroMed, Inc., Cleveland, OH.

The Post-Op back book—taking charge of your recovery from Surgery, 2000, 16 pgs., the Stay Well Company, San Bruno, CA.

University$^{AM}$ Plate—Titanium Anterior System—Ordering Information for implants and instruments, 1996, 6 pgs., AcroMed, Inc., Cleveland, OH.

* cited by examiner

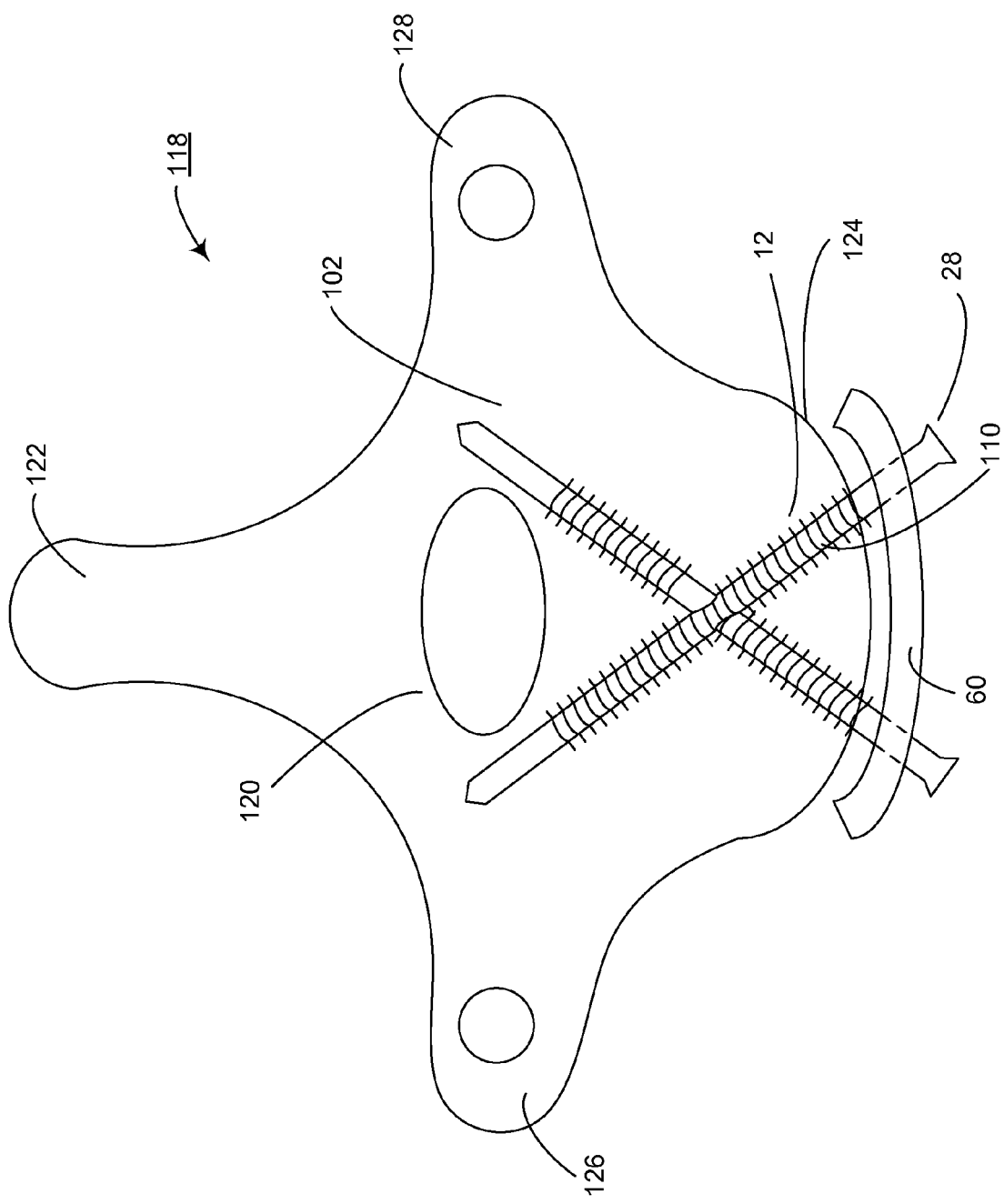

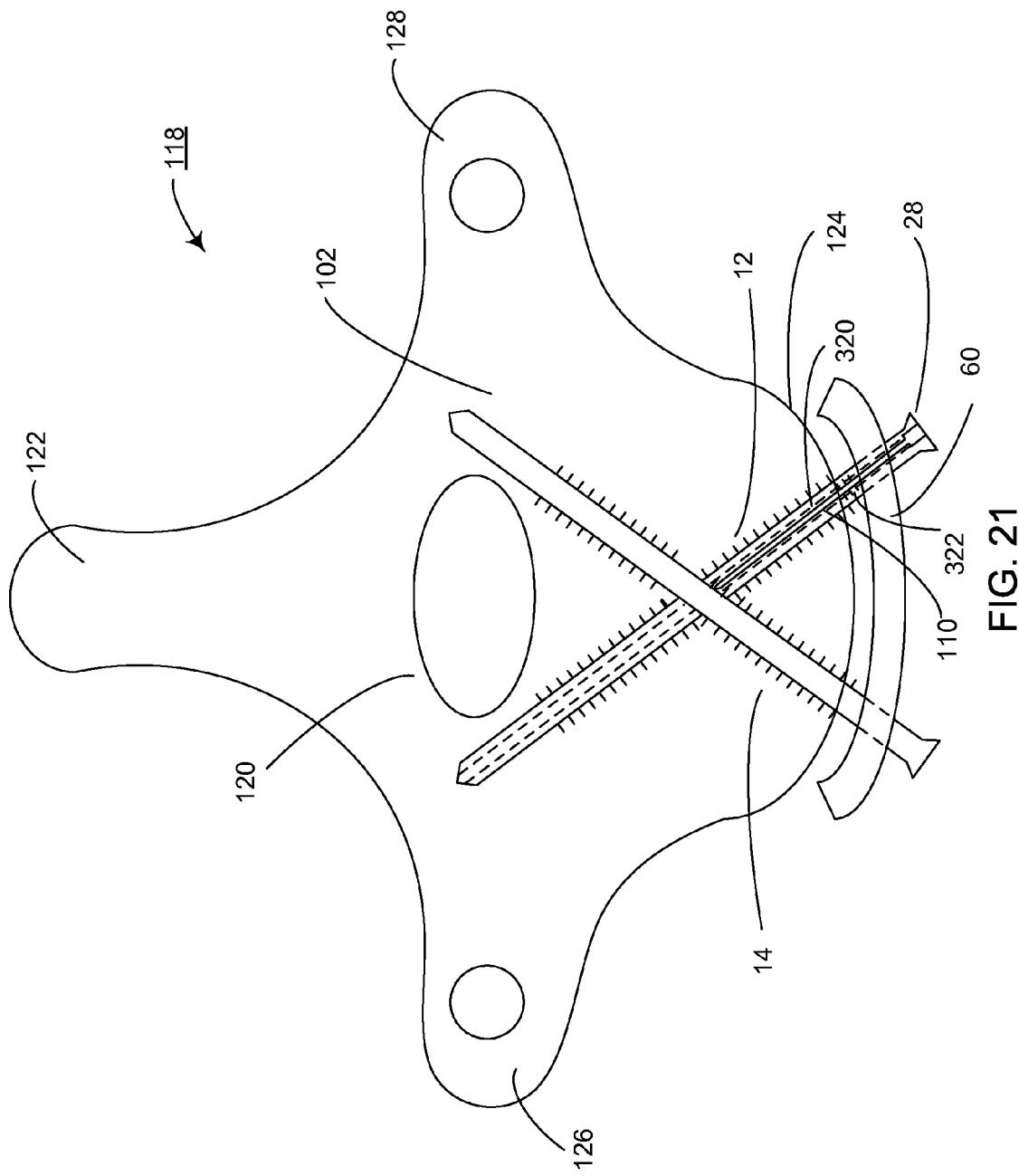

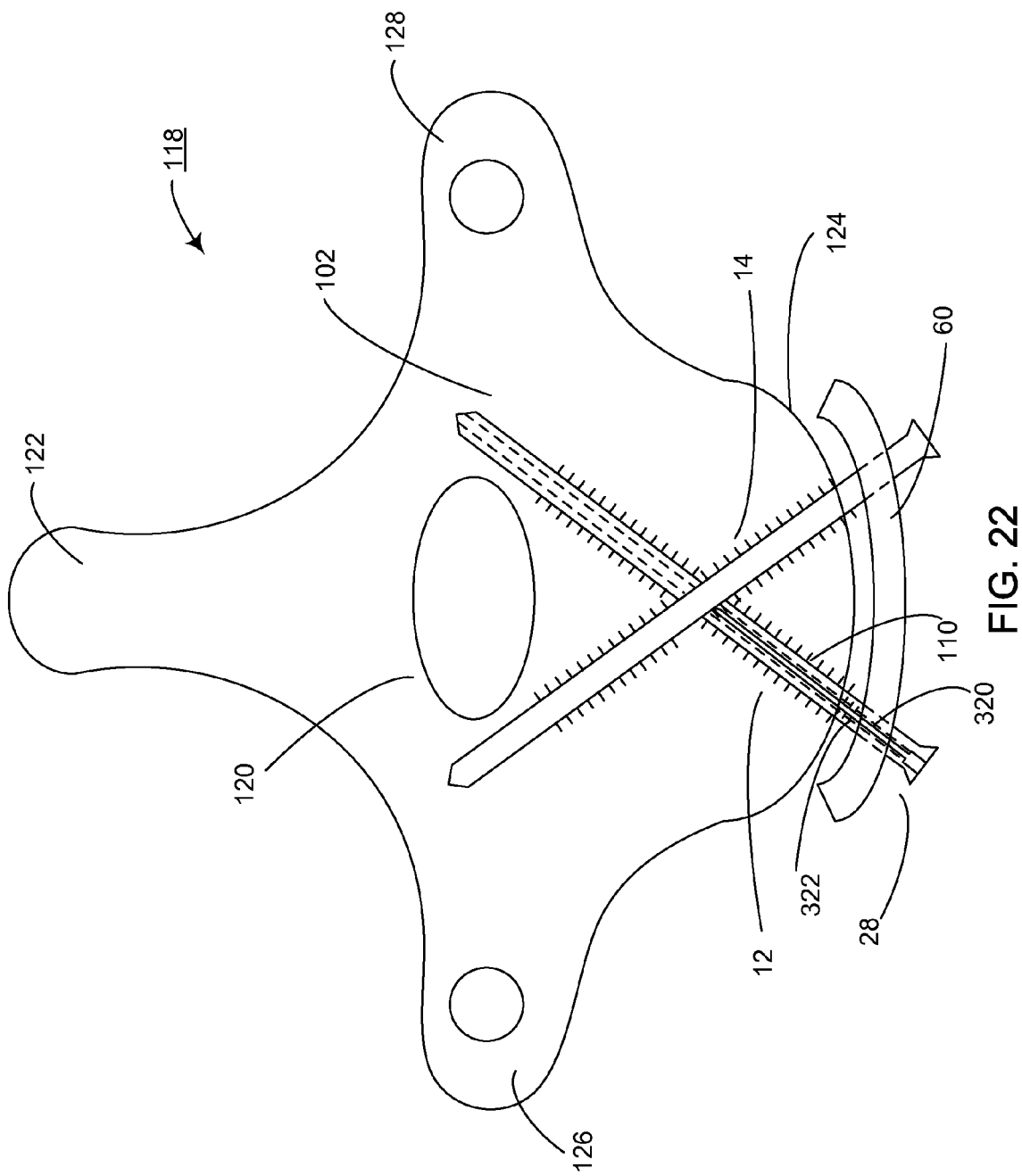

VERTEBRAL SCREW ARRANGEMENT WITH LOCKING PIN

CROSS-REFERENCE TO RELATED APPLICATIONS

This patent application is a continuation-in-part of U.S. patent application Ser. No. 11/935,932, filed Nov. 6, 2007, which is hereby incorporated by reference herein in its entirety.

FIELD OF THE DISCLOSURE

The present disclosure relates generally to spinal stabilization and correcting spinal deformities. More specifically, but not by way of limitation, the present disclosure relates to a vertebral screw arrangement with locking pin.

BACKGROUND OF THE DISCLOSURE

The human spine frequently requires surgery to repair deformities or injuries. Spinal problems may be caused by a trauma to the spine received during an accident, excessive strain or stress on the spine from physical activities, a sedentary lifestyle and poor posture that may place abnormal pressure on the spine, disease or a variety of other reasons. Spinal fusion is a common surgery intended to alleviate pain caused by these spinal deformities or injuries.

The spinal fusion procedure generally includes removing a disk, packing a bone graft between vertebrae and placing a spinal implant, such as screws attached to a plate, rod or cage, to fuse elements of the spine together. Once the disk is removed and the bone graft is placed between the vertebrae, the bone graft will fuse to the vertebrae over a period of several months following the surgery.

The purpose of the plate is to stabilize the vertebrae until the bone graft has become fused to the vertebrae. The plate is positioned to extend between at least two vertebrae. The plate is attached to screws anchored in each of the adjacent vertebrae, thus immobilizing the desired portion of the spine. The plate is anchored to the screws either on the front, anterior, or back, posterior, sides of the vertebrae.

Procedurally, anterior, or entry from the neck region of the patient, cervical vertebra surgery provides the surgeon with optimum access to the entire intervertebral disk. Posterior, or entry from the back of the patient, surgery is less preferred since access to the disk is restricted. Once the anterior cervical discectomy, or removal of the cervical disk, is completed, the bone graft is placed into the space between the vertebrae previously occupied by the disk. The patient is then positioned for anterior cervical fusion, or placement, of the plate.

One particular anterior cervical fusion technique is accomplished by securing fixation screws in the vertebral body. Rods and/or plates are then engaged between the screws in superior and inferior vertebral bodies. Normally, two screws are placed in each body. Therefore, two rods and/or plates are needed between the vertebrae. The rods and/or plates and screws thereby stabilize the cervical vertebrae and provide time for the vertebrae and bone graft to fuse into a solitary unit.

However, anterior cervical fusion has caused increased operative morbidity due to the very difficult nature of the procedure. Moreover, many of the anterior cervical fusion techniques have problems of potential risk to a surrounding vascular network and in completely clearing the adjacent spinal canal. Furthermore, most of the anterior cervical fusion techniques rely on support from the vertebral body only and therefore cannot be used in an extremely osteoporotic spine because vertebral body strength is not sufficient.

Several plating systems have been developed for anterior internal fixation of the spine. Among these plating systems, a Syracuse I-plate provides a number of differently sized I-shaped plates which are engaged across a burst fracture. However, the Syracuse I-plate does not allow for compression or distraction of a bone graft between the superior and inferior vertebrae. A Stafix plating system, provided by Duma International of Taipei, Taiwan, includes a plate that has a number of screw holes and a single screw slot. The Stafix plate permits quadrilateral placement of bone screws, but not compression or distraction. Moreover, the Stafix plate, as with the above-mentioned anterior plates, cannot provide rigid or semi-rigid fixation using bone screws or bone bolts.

Thus, a need exists for a vertebral screw arrangement that obtains the benefits while overcoming the disadvantages of prior procedures and systems.

SUMMARY OF THE DISCLOSURE

Brief Description of the Drawings

For a more complete understanding of the present disclosure and the advantages thereof, reference is now made to the following brief description, taken in connection with the accompanying drawings and detailed description, wherein like reference numerals represent like parts, in which:

FIG. 20 is a top plan view of the pedicle screws, illustrated in FIGS. 13 and 14, shown anteriorly positioned in a vertebra in accordance with an embodiment of the present disclosure;

FIG. 21 illustrates alignment of the second pedicle screw utilizing the guide member for attachment of the pedicle screw positioned within the vertebra, according to one aspect of the present disclosure;

FIG. 22 illustrates a left side anterior positioning of the pedicle screw and alignment of the second pedicle screw utilizing the guide member according to yet another aspect of the present disclosure;

DETAILED DESCRIPTION OF EMBODIMENTS

It should be understood at the outset that although exemplary implementations of the present disclosure are illustrated below, the present disclosure may be implemented using any number of techniques, whether currently known or in existence. The present disclosure should in no way be limited to the exemplary implementations, drawings, and techniques illustrated below, including the exemplary designs and implementations illustrated and described herein.

The present disclosure is not intended to be limited to applications in a specific region of the spine, and may, in fact, be utilized equally well with the cervical, thoracic, lumbar and sacrum vertebrae of the spine. However, for purposes of explanation, the surgical procedure will be discussed in greater detail with respect to the cervical, lumbar, or thoracic vertebrae region of the spine.

Figure 1:
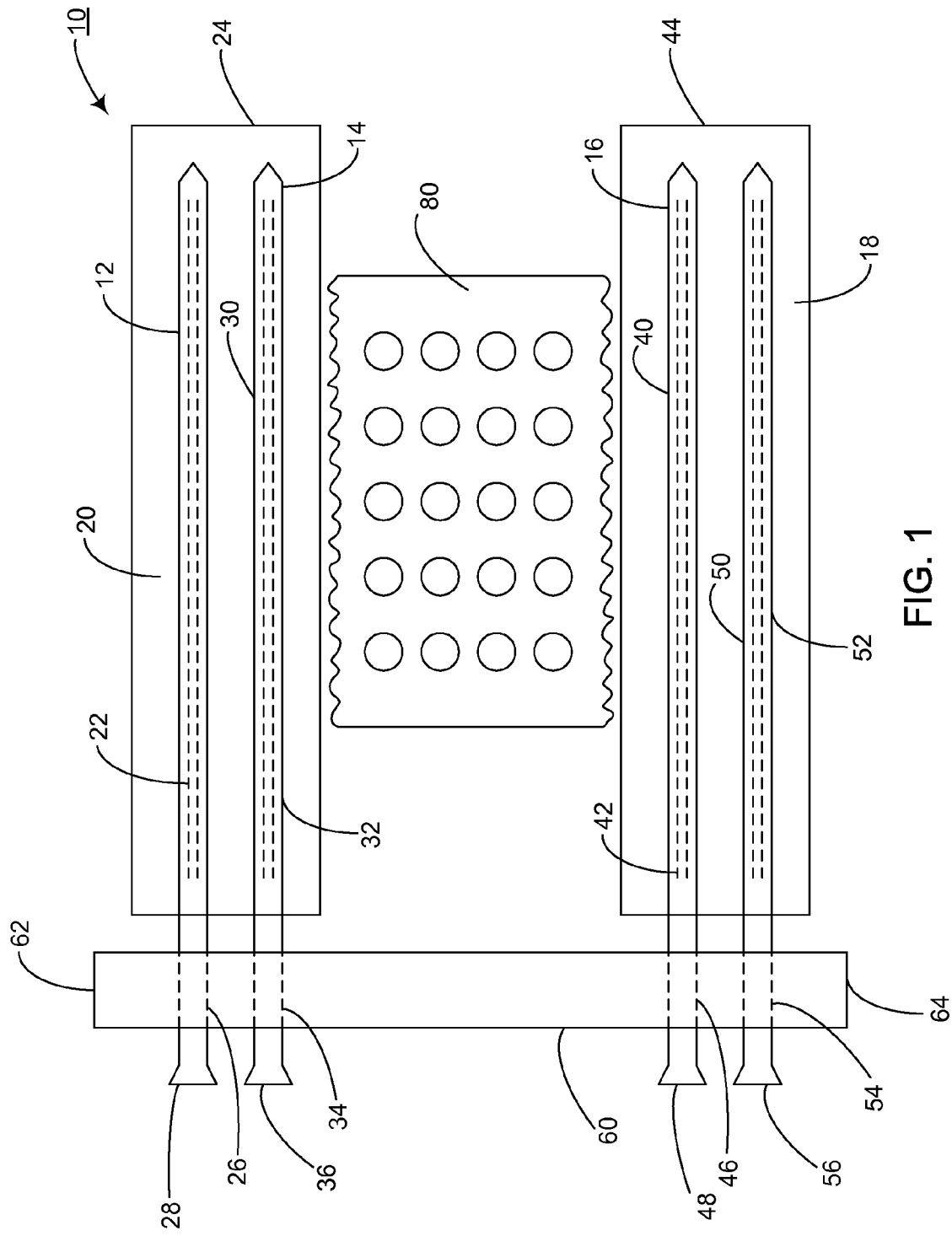
FIG. 1 is a perspective view of a vertebral stabilization assembly illustrated partially in phantom and shown stabilizing an upper and lower vertebra according to one aspect of the present disclosure.

FIG. 1 illustrates one aspect of the vertebral stabilization assembly 10 constructed in accordance with the present disclosure. The vertebral stabilization assembly 10 is an innovative device for stabilizing a plurality of vertebrae of the spine. The vertebral stabilization assembly 10 includes a first pedicle screw 12, a second pedicle screw 14, a third pedicle screw 16 and a fourth pedicle screw 18. The first pedicle screw includes a shaft 20 provided with a threaded portion 22. The threaded portion 22 of the shaft 20 is operable for threading engagement of the first pedicle screw 12 with a first vertebra 24. The shaft 20 of the pedicle screw 12 further includes an engaging portion 26.

The second pedicle screw 14 is substantially similar to the first pedicle screw 12 in that the second pedicle screw 14 includes a shaft 30 provided with a threaded portion 32. The threaded portion 32 of the shaft 30 is operable for threading engagement of the second pedicle screw 14 with the first vertebrae 24. The shaft 30 of the second pedicle screw 14 is provided with an engaging portion 34.

The third pedicle screw 16 is substantially similar to the first pedicle screw 12 in that the third pedicle screw 16 includes a shaft 40 provided with a threaded portion 42. The threaded portion 42 of the shaft 40 is operable for threading engagement of the third pedicle screw 16 with a second vertebra 44. The shaft 40 of the third pedicle screw 16 is provided with an engaging portion 46.

The fourth pedicle screw 18 is also substantially similar to the first pedicle screw 12 in that the fourth pedicle screw 18 includes a shaft 50 provided with a threaded portion 52. The threaded portion 52 of the shaft 50 is operable for threading engagement of the fourth pedicle screw 18 with the second vertebrae 44. The shaft 50 of the fourth pedicle screw 18 is provided with an engaging portion 54.

The shafts 20, 30, 40 and 50 of the first, second, third and fourth pedicle screws 12, 14, 16 and 18 are of appropriate length to sufficiently anchor the first, second, third, and fourth pedicle screws 12, 14, 16 and 18 in the first and second vertebrae 24 and 44, respectively. The threaded portions 22, 32, 42 and 52 of the first, second, third and fourth pedicle screws 12, 14, 16 and 18 may be threads similar to those on ordinary screws and extending a distance along the shafts 20, 30, 40 and 50 sufficient to promote optimum anchoring of the first, second, third and fourth pedicle screws 12, 14, 16 and 18 within the first and second vertebrae 24 and 44, respectively. The first, second, third and fourth pedicle screws 12, 14, 16 and 18 are preferably constructed of a substantially rigid material such as, but not limited to, titanium, steel, metal, metal alloys, polymeric material, or a variety of other substantially rigid materials adapted to promote rigid engagement of the first, second, third and fourth pedicle screws 12, 14, 16 and 18 to the first and second vertebrae 24 and 44, respectively.

The vertebral stabilization assembly 10 further includes a connecting member 60 having a beveled shape which conforms to the contour of an anterior side of the vertebrae 24 and 44. The connecting member 60 has a first end 62 and a second end 64. The first end 62 of the connecting member 60 is coupled to the first and second pedicle screws 12 and 14. The second end 64 of the connecting member 60 is coupled to the third and fourth pedicle screw 16 and 18. This arrangement enables stabilization of the first and second vertebrae 24 and 44.

The connecting member 60 may be constructed from a variety of substantially rigid materials, possibly similar to that of the pedicle screws 12, 14, 16 and 18, such as, but not limited to, titanium, steel, metal, metal alloys, polymeric material, or other substantially rigid materials suitable for stabilization of the first and second vertebrae 24 and 44 by coupling to the first, second, third and fourth pedicle screws 12, 14, 16 and 18. Furthermore, a head 28, 36, 48 and 56 may be provided for the first, second, third, and fourth pedicle screws 12, 14, 16 and 18, respectively.

Figure 2:
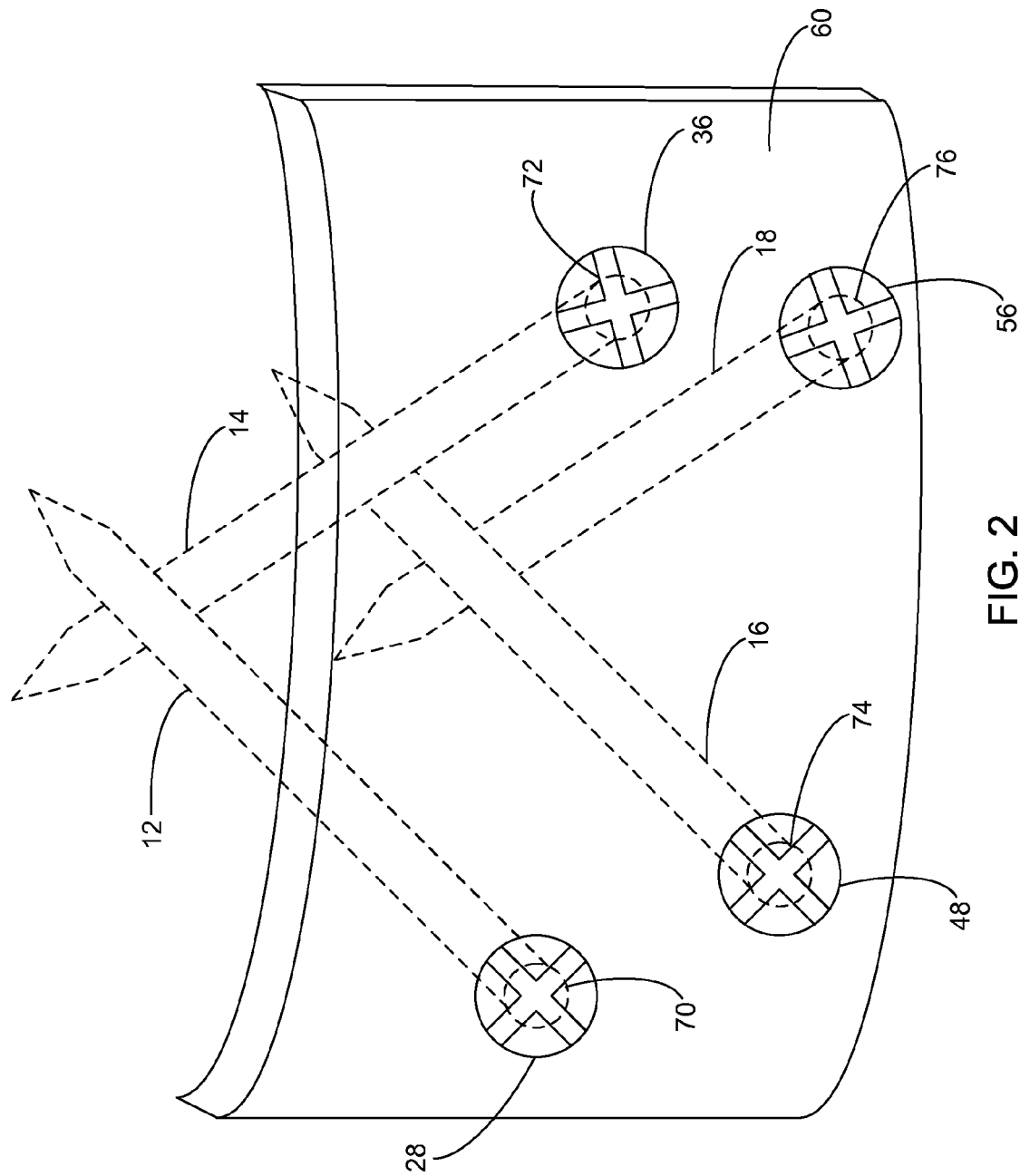
FIG. 2 is a perspective view of the vertebral stabilization assembly, as shown in FIG. 1, constructive in accordance with an embodiment of the present disclosure.

FIG. 2 illustrates the vertebral stabilization assembly 10, substantially as shown in FIG. 1, with the first and second vertebrae 24 and 44 removed from the illustration for the purpose of further describing the present disclosure. As mentioned above, the first, second, third and fourth pedicle screws 12, 14, 16 and 18 are provided with a head 28, 36, 48 and 56 respectively. The heads 28, 36, 48 and 56 of the first, second, third and fourth pedicle screws 12, 14, 16 and 18 may be configured to receive a tool, such as, but not limited to, drill guide, a standard flat or a Phillips-head screw driver, Allen or other wrench connection, or a variety of male to female or female to male mating configurations for threadingly engaging the first, second, third and fourth pedicle screws 12, 14, 16 and 18 into the first and second vertebrae 24 and 44.

In other embodiments (not shown) the heads 28, 36, 48 and 56 of the first, second, third and fourth pedicle screws 12, 14, 16 and 18 may be configured unlike the head of a standard screw and instead unitarily formed, for example, rectangularly from the shafts 20, 30, 40 and 50 for mating engagement with a unique tool such as a drill guide and adapted to receive the rectangularly-formed shaft.

It will be appreciated that a variety of constructions and configurations of the heads 28, 36, 48 and 56 of the first, second, third and fourth pedicle screws 12, 14, 16 and 18 will readily suggest themselves to one of ordinary skill in the art and may be provided in numerous configurations such that a tool may be attached temporarily to the heads 28, 36 48 and 56 for imparting a rotation upon the first, second, third and fourth pedicle screws 12, 14, 16 and 18.

In the present illustration, the engaging portion 26 of the shaft 20 can be more easily seen as adapted to engage a first hole 70 of the connecting member 60. The first hole 70 may be a threaded opening formed in the connection member 60 and adapted to receive a threaded engaging portion 26 of the first pedicle screw 12. In this manner the first pedicle screw 12 threadingly engages the first hole 70 to achieve a rigid locking connection between the first pedicle screw 12 and the connecting member 60.

The engaging portion 34 of the shaft 30 may be adapted to engage a second hole 72 of the connecting member 60. The second hole 72 may be substantially similar to the first hole 70 in that the second hole 72 may include a threaded opening formed in the connection member 60. The second pedicle screw 14 may threadingly engage the second hole 72 to achieve a rigid locking connection between the second pedicle screw 14 and the connecting member 60. The second hole 72 may be offset in the vertical direction either up or down from the first hole 70.

Also, the engaging portion 46 of the shaft 40 may be adapted to engage a third hole 74 of the connecting member 60. The third hole 74 may also be substantially similar to the first hole 70 in that the third hole 74 may include a threaded opening formed in the connection member 60. The third pedicle screw 16 may threadingly engage the third hole 74 to achieve a rigid locking connection between the third pedicle screw 16 and the connecting member 60.

Further, the engaging portion 54 of the shaft 50 may be adapted to engage a fourth hole 76 of the connecting member 60. The fourth hole 76 may also be substantially similar to the first hole 70 in that the fourth hole 76 may include a threaded opening formed in the connection member 60. The fourth pedicle screw 18 may threadingly engage the fourth hole 76 to achieve a rigid locking connection between the fourth pedicle screw 18 and the connecting member 60. The fourth hole 76 may be offset in the vertical direction either up or down from the third hole 74.

In other embodiments (not shown), the holes 70, 72, 74 and 76 may be a tension connection opening in the connecting member 60 for receiving and engaging in a tensioning fashion the engaging portions 26, 34, 46 and 54 of the first, second, third and fourth pedicle screws 12, 14, 16 and 18, respectively. In yet other embodiments (not shown), the holes 70, 72, 74 and 76 may include a locking assembly adapted to receive the engaging portions 26, 34, 46 and 54 of the first, second, third and fourth pedicle screws 12, 14, 16 and 18 and lock them into place upon insertion. The locking engagement of the holes 70, 72, 74 and 76 may be accomplished in a variety of manners including a keyed design of the holes 70, 72, 74 and 76 such that when the engaging portions 26, 34, 46 and 54 of the first, second, third and fourth pedicle screws 12, 14, 16 and 18 are inserted into the holes 70, 72, 74 and 76, they are locked into place upon rotation of the first, second, third and fourth pedicle screws 12, 14, 16 and 18.

Yet in other embodiments (not shown), the holes 70, 72, 74 and 76 may be modified to outer surfaces of the shafts 20, 30, 40 and 50 of the first, second, third and fourth pedicle screws 12, 14, 16 and 18 such that the holes 70, 72, 74 and 76 of the connecting member 60 may be adapted to receive the engaging portions 26, 34, 46 and 54 of the shafts 20, 30, 40 and 50 within the opening of holes 70, 72, 74 and 76 of the connecting member 60. In this manner, the locking or tensioning mechanism may be retained by the holes 70, 72, 74 and 76 of the connecting member 60 for engaging the first, second, third and fourth pedicle screws 12, 14, 16 and 18.

A number of other connections including spring, ball, or other tensioning connections, as well as, threading, locking, and other mating connections for engaging the holes 70, 72, 74 and 76 of the connecting member 60 with the engaging portions 26, 34, 46 and 54 of the shafts 20, 30, 40 and 50 of the first, second, third and fourth pedicle screws 12, 14, 16 and 18 will readily suggest themselves to one of ordinary skill in the art and are within the spirit and scope of the present disclosure. It will be appreciated that the engaging portions 26, 34, 46 and 54 of the shafts 20, 30, 40 and 50 of the first, second, third and fourth pedicle screws 12, 14, 16 and 18 all may be constructed substantially identical.

Further yet in other embodiments (not shown), the connecting member 60 may include holes for engaging temporary holding screws that fixate the connecting member 60 to the first and second vertebrae 24 and 44 in order to allow a precise drilling while preventing the movement of the connecting member 60.

Figure 3:
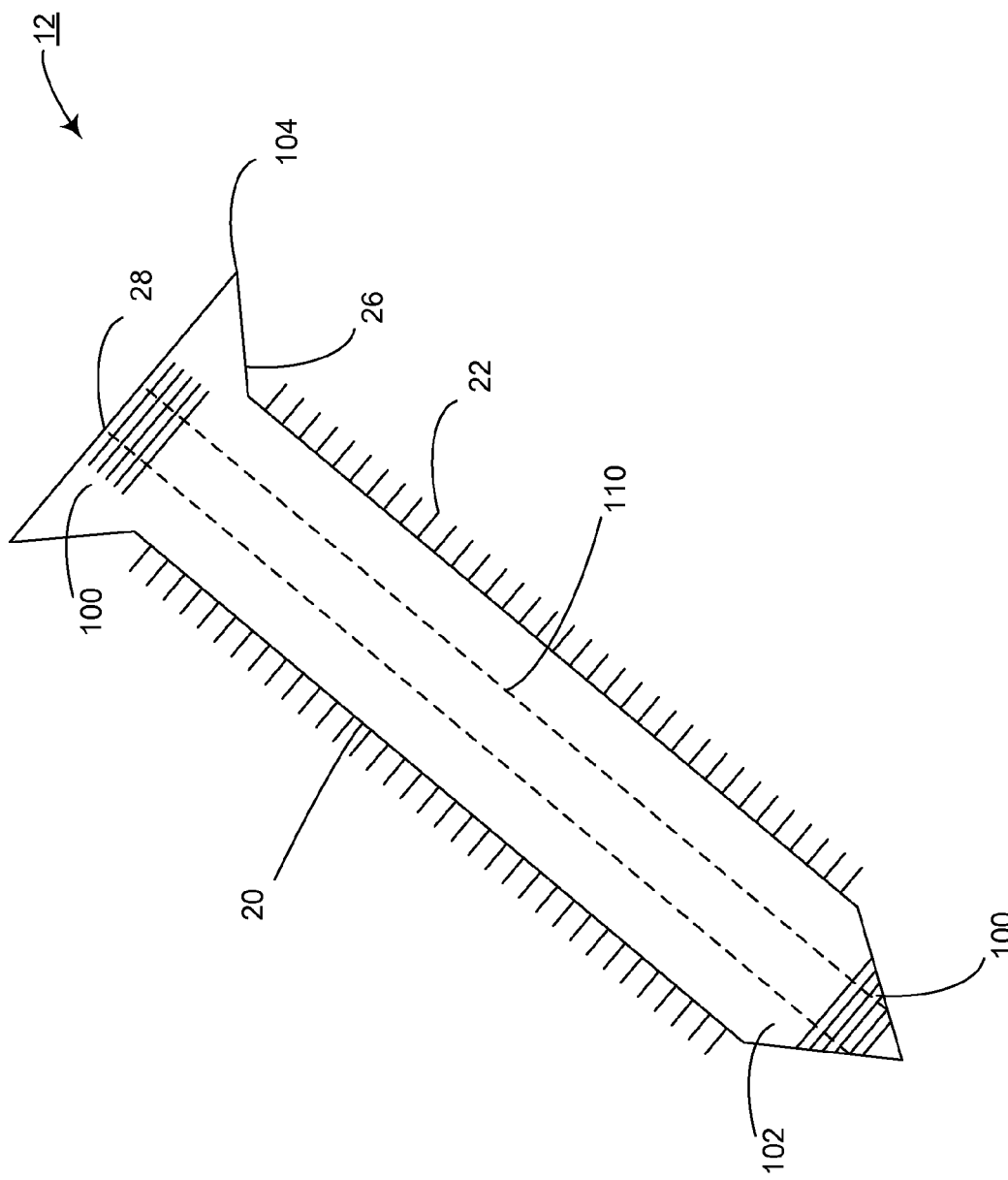
FIG. 3 is a side elevational view of a pedicle screw according to one aspect of the present disclosure.

FIG. 3 illustrates another aspect of the present disclosure of a pedicle screw, such as the pedicle screw 12, of the vertebral stabilization assembly 10 of the present disclosure. In this aspect the pedicle screw 12, as well as having the shaft 20 having the threaded portion 22 and the engaging portion 26, as previously discussed, further includes a coupling portion 100 provided on both ends of the shaft 20. Also, the pedicle screw 12 may be provided with a cannulated shaft 20 such that a passageway 110 extends through the shaft 20 from the head 28 to the distal end 102 of the shaft 20.

The coupling portion 100 is adapted to connect a guide member (which will be discussed in greater detail with reference to FIG. 5) of the vertebral stabilization assembly. In one aspect the coupling portion 100 may be a threaded portion on the outer surface of the shaft 20 near the distal end 102 of the shaft 20. In another aspect, the coupling portion 100 may be a threaded portion on the inner surface of the shaft 20 near an engaging end 104 of the shaft 20. The guide member may be threadingly connected to the coupling portion 100 about the distal end 102 and/or the engaging end 104 of the shaft 20. In other embodiments, however, the coupling portion 100 may be an opening provided in the distal end 102 and/or engaging end 104 of the shaft 20 such that a portion of the guide member may be threadingly received within the opening in the distal end 102 and/or engaging end 104 of the shaft 20 for threading engagement therewith the coupling portion 100.

As previously mentioned, the engaging portion 26 of shaft 20 is operable to engage the connecting member 60. As previously discussed, this rigid engagement may be provided in a variety of manners, such as, but not limited to, a locking engagement, a threading engagement, and a tensioning or other rigid coupling connection of the connecting member 60 with the first pedicle screw 12 about the engaging portion 26.

Figure 4:
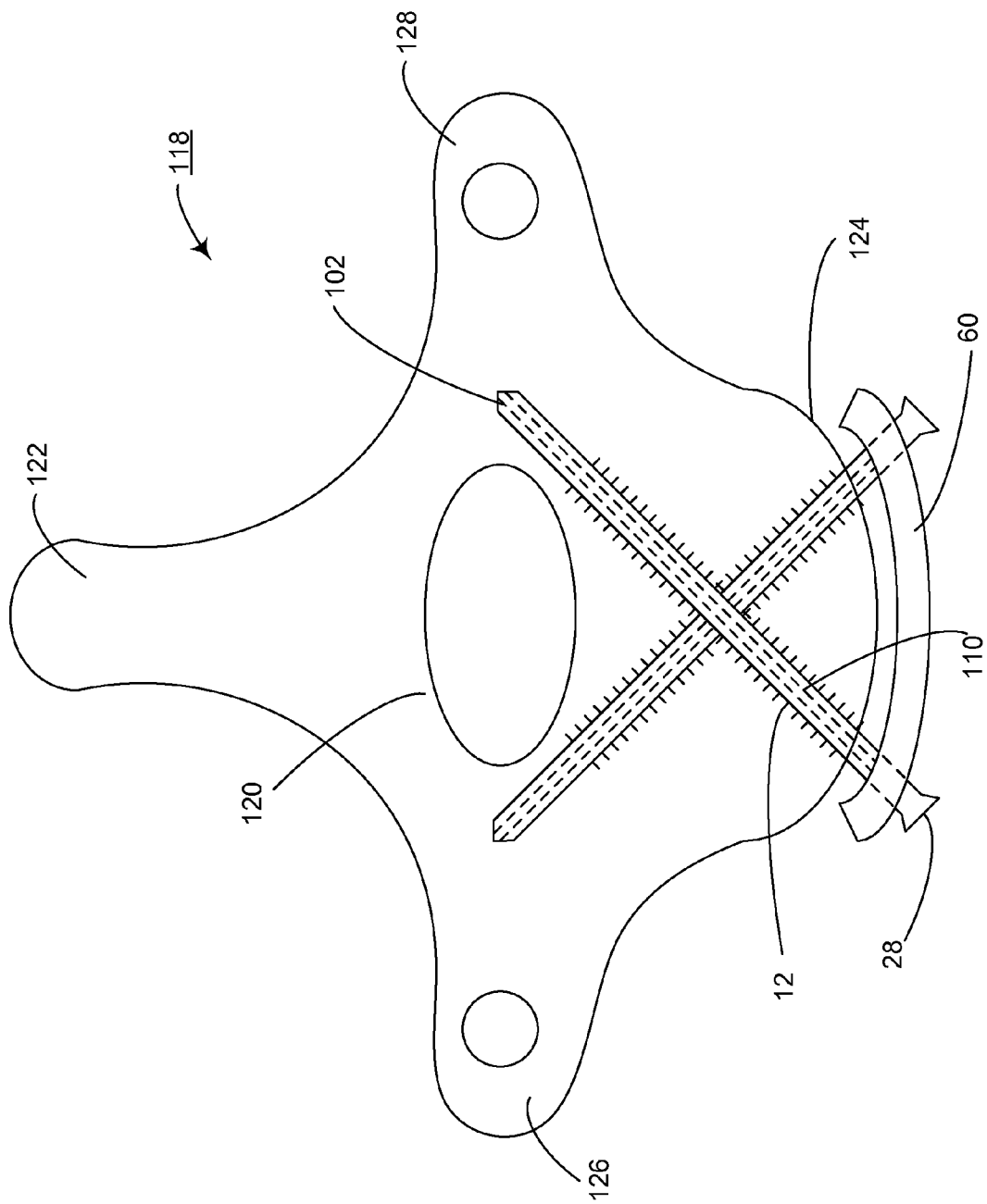
FIG. 4 is a top plan view of the pedicle screw, illustrated in FIG. 3, shown anteriorly positioned in a vertebra in accordance with an embodiment of the present disclosure.

Referring also to FIG. 4 a top view of a vertebra 118, such as a cervical, a lumbar, or a thoracic vertebra, is shown with the first pedicle screw 12 set therein. One advantage of the present disclosure is that the first pedicle screw 12 may be placed through a pedicle 120 on an anterior side 124 of the vertebra 118.

Anterior placement to the pedicle 120 of the vertebra 118 provides a surgeon with full access to the disc area. Anterior placement also is capable of distributing compressive loads to the vertebral support members 10 from rotational and translational movement, and preventing displacement of graft material.

As previously mentioned, the connecting member 60 is positionable on the anterior side 124 of the vertebra 118. Thus, the vertebral stabilization assembly 10 of the present disclosure achieves the advantages of anterior vertebral stabilization, since the connecting member 60 is positioned on the anterior side 124 of the vertebra 118.

The first pedicle screw 12 may be placed in the vertebra 118 anteriorly avoiding the disadvantages associated with large, invasive posterior procedures which require significant interference and dissection of adjacent muscles.

In yet another aspect of the present disclosure, the first pedicle screw 12 may be provided with a cannulated shaft 20 such that a passageway 110 extends through the shaft 20 from the head 28 to the distal end 102 of the shaft 20. By utilizing the passageway 110 extending through the shaft 20 of the first pedicle screw 12, a tool (not shown) such as a tap or drill bit may be placed through this cannulated portion of the shaft 20 such that the tool or drill bit may enter near the head 28 of the first pedicle screw 12. The tool may then be extended through the passageway 110 towards the distal end 102.

The tool may then be utilized to drill through to a posterior side 122 of the vertebra 118 for location of the distal end 102 of the pedicle screw 12 from the posterior side 122 of the vertebra 118. Since only a small distance must be drilled, there is minimal risk to damages to other parts of the vertebra 118. Furthermore, once the tool penetrates the posterior side 122 of the vertebra 118, the surgeon should be able to sense the reduced resistance and friction on the tool. Furthermore, the tool may be provided with stops or a drill bit may be cannulated to prevent extension of the drill bit beyond the posterior side 122 of the vertebra 118.

In the present embodiment, right side 128 placement of the first pedicle screw 12 is preferable to avoid injuries to the patient by utilizing a shorter screw with similar construction as of the first pedicle screw 12 to drill into vertebra 118. In some instances, however, left side 126 placement of the first pedicle screw 12 in the vertebra 118 will be necessary. Left side 126 placement of the first pedicle screw 12 will be discussed in greater detail with reference to FIG. 7.

Figure 5:
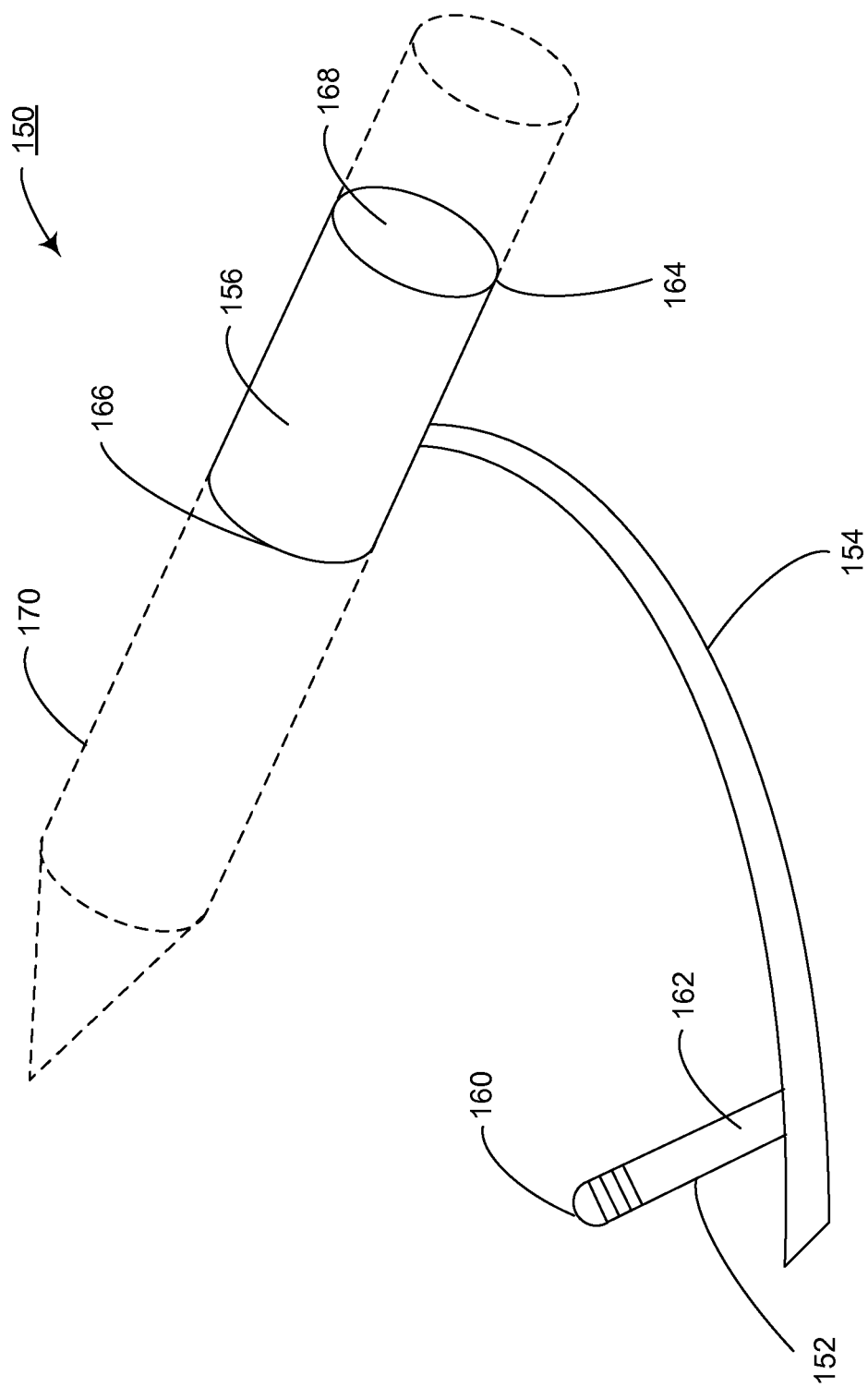
FIG. 5 is a perspective view of a guide member according to one aspect of the present disclosure for aligning a second pedicle screw shown in phantom.

FIG. 5 illustrates a guide member 150 in accordance with yet another aspect of the present disclosure. The guide member 150 includes a coupling portion 152 an offset member 154 and an alignment member 156. The coupling portion 152 is operable to couple with the coupling portion 100 of the first pedicle screw 12 (see FIG. 3). The offset member 154 is connected to the coupling portion 152. The offset member 154 extends from the coupling portion 152 relative to the connection of the coupling portion 152 to the coupling portion 100 of the first pedicle screw 12. The alignment member 156 is connected to the offset member 154. The alignment member 156 is operable for alignment of another pedicle screw, such as the second and/or fourth pedicle screws 14 and 18, relative to a portion of the first and/or third pedicle screw 12 and 16, such as the engaging end 104.

The guide member 150 may be constructed from a variety of materials such as, but not limited to, titanium, steel, metal or other metal alloys, a substantially rigid polymeric material, aluminum or other substantially rigid materials sufficient for these purposes. The coupling portion 152 is provided with a first end 160 and a second end 162. The first end 160 of the coupling portion 152 may be threaded for threading engagement to the coupling portion 100 of the first pedicle screw 12.

It should be appreciated, however, that a number of connecting methods may be utilized to accomplish the connection of the first end 160 of the coupling portion 152 to the coupling portion 100 of the first pedicle screw 12. For example, the first end 160 may be shaped so as to be substantially rectangular or have another geometric shape about a portion of the first end 160 such that a similarly geometrically configured opening in the coupling portion 100 in the engaging end 104 of the first pedicle screw 12 is adapted to receive the first end 160 of the coupling portion 152. Other locking or tensioning engagements of the first end 160 of the coupling portion 152 to the coupling portion 100 of the first pedicle screw 12, as well as a variety of other methods for achieving this attachment, will readily suggest themselves to one of ordinary skill in the art and are within the spirit and scope of the present disclosure.

The second end 162 of the coupling portion 152 is attached to the offset member 154. The attachment of the coupling portion 152 to the offset member 154 may be accomplished by a threading or tensioning or locking connection, or may be accomplished by a welded or bonded connection of the second end 162 of the coupling portion 152 to the offset member 154. Although welding or bonding engagements of various components of the vertebral stabilization assembly 10 of the present disclosure are preferable, it should be appreciated that bonding or other gluing or tacking materials may be used for this connection and satisfactory for these purposes.

The offset member 154 is shown as a substantially arcuate member extending from the second end 162 of the coupling portion 152 to the alignment member 156. However, in other embodiments, one of which is described hereinafter, the alignment member 156 may be comprised of a number of foldable or extendable or hinging segments to promote use within the confinements of a patient's anterior side. While the offset member 154 is shown as a substantially rigid arcuate member, a number of other configurations of the offset member 154, such as a substantially straight member, or a stair-stepped member, as well as the offset member 154 being comprised of several connectable or extendable members are contemplated according to other aspects (not shown) of the present disclosure.

A number of configurations of the offset member 154, such as formation of a portion of the offset member 154 unitarily with the coupling portion 152 and formation of a remaining portion of the offset member 154 unitarily formed with the alignment member 156 may also be utilized for these purposes. Although the offset member 154 is shown in a preferred aspect, a variety of configurations of the offset member 154 will readily suggest themselves to one of ordinary skill in the art for positioning the alignment member 156 relative to a portion of the first pedicle screw 12 when the coupling portion 152 of the guide member 150 is connected to the coupling portion 100 of the first pedicle screw 12 and are within the spirit and scope of the present disclosure and will not be discussed in further detail for the purposes of brevity.

The alignment member 156 is rigidly connected to the offset member 154 by welding or bonding or other similar means. However, attachment of the alignment member 156 to the offset member 154 may be accomplished by a threading, locking or tensioning engagement and is satisfactory for these purposes. The alignment member 156 is a substantially tubular member having a first end 164 and a second end 166 and an opening 168 extending through from the first end 164 to the second end 166.

The alignment member 156 is provided such that the opening 168 is of a sufficient diameter to receive a drilling device 170, shown in phantom, through the opening 168 for alignment with the engaging portion 26 on the shaft 20 of the first pedicle screw 12. The drilling device 170 may be the bit of a drill or other devices operative to drill an opening into vertebral bone. Thus, the alignment member 156 receives the drilling device 170 that drills an opening properly aligned for crossing, but not intersecting, the second pedicle screw 14 relative to the first pedicle screw 12. Thus, the guide member 150 is advantageously provided for creating an drilled hole in vertebra 118 offset in the vertical direction from the first pedicle screw 12.

It should be appreciated that while the alignment member 156 of the present aspect is illustrated as a substantially tubular member having an opening 168, in other embodiments the alignment member 156 may not be a completely tubular, and instead, may be provided as a guide or positioning member for alignment of the crossing, but not intersecting, the second pedicle screw 14 relative to the first pedicle screw 12.

Numerous configurations for offsetting the second pedicle screw 14 in the vertical direction from the first pedicle screw 12 may be utilized for these purposes and will readily suggest themselves to one of ordinary skill in the art and are within the spirit and scope of the present disclosure and will not be discussed further for purposes of brevity.

Figure 6:
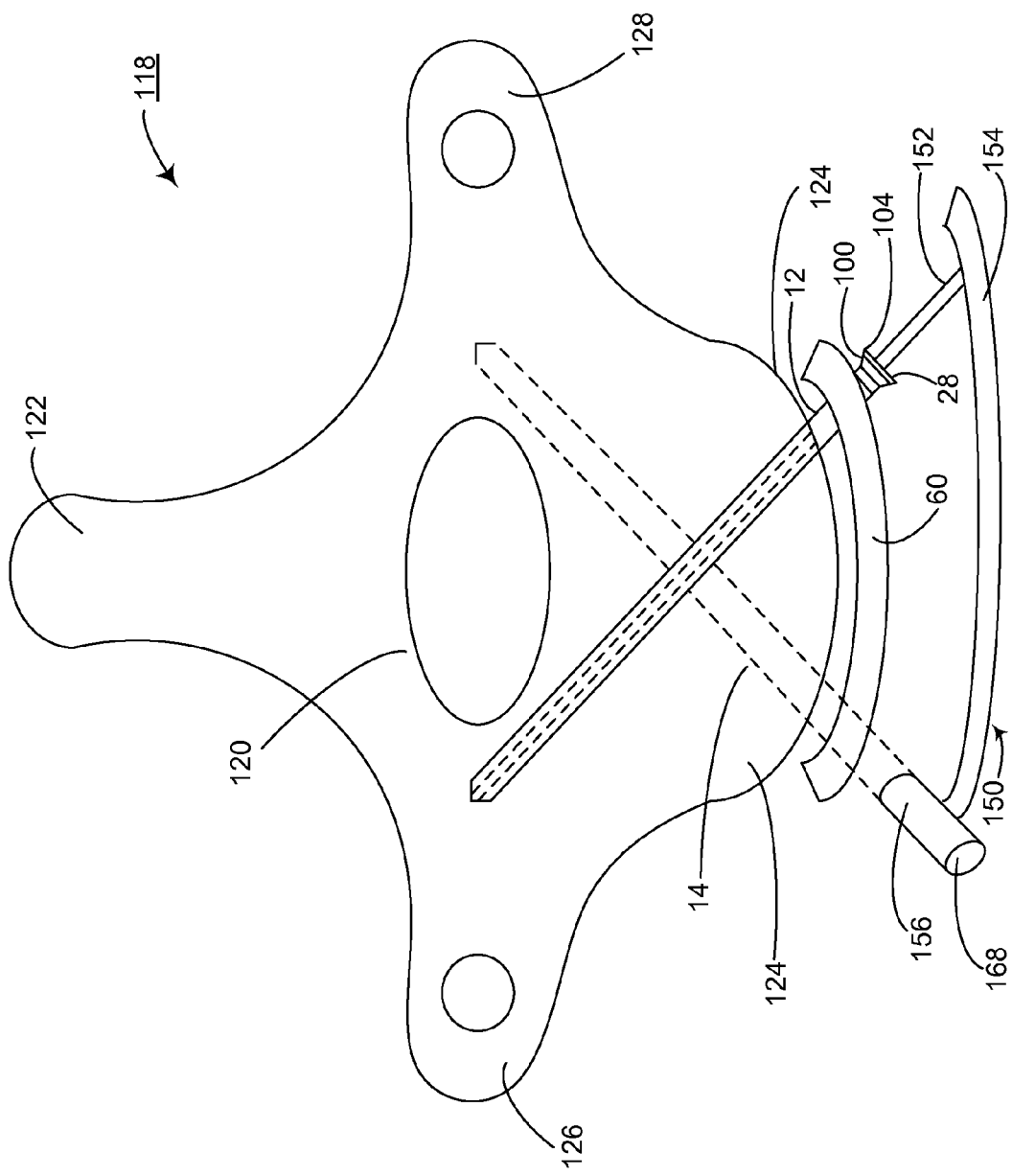
FIG. 6 illustrates alignment of the second pedicle screw utilizing the guide member for attachment of the pedicle screw positioned within the vertebra, as shown in FIG. 4, according to one aspect of the present disclosure.

FIG. 6 illustrates a top view of the vertebra 118 shown with the first pedicle screw 12 positioned therein with the guide member 150 shown attached to the first pedicle screw 12. In this view, it can be seen that the guide member 150 is a useful tool for placement of the second pedicle screw 14 (shown in phantom). It will be appreciated that, procedurally, the first pedicle screw 12 has been placed through the anterior side 124 of the vertebra 118.

At this point, the guide member 150 may be positioned such that the coupling portion 152 of the guide member 150 is connected to the coupling portion 100 of the first pedicle screw 12. An innovative aspect of the pedicle screw 12 is that the coupling portion 100 on the engaging end 104 of the first pedicle screw 12 is associated with the placement of the second pedicle screw 14. The association of the coupling portion 100 of the first pedicle screw 12 and placement of the second pedicle screw 14 is a significant advantage of the first pedicle screw 12 according to the present disclosure. That is, this association allows for the guide member 150 to be configured relative to this association. Thus, the coupling portion 152 of the guide member 150, when coupled to the first pedicle screw 12, aligns the alignment member 156 for the appropriate placement of the second pedicle screw 14. Utilizing the guide member 150, several methods exist for properly aligning the second pedicle screw 14. It may be preferable to utilize the drilling device 170 to create an opening in the anterior side 124 of the vertebra 118. Thereafter, the guide member 150 may be removed and the second pedicle screw 14 disposed in the opening drilled in the vertebra 118.

In some instances, it may be beneficial for the alignment member 156 to be adapted to receive the second pedicle screw 14 positioned to extend through the opening 168 of the alignment member 156. The second pedicle screw 14 may then be drilled or threaded directly into the left side 126 of the anterior side 124 of the vertebra 118. Whether an opening is first drilled or the second pedicle screw 14 is directly drilled into the vertebra 118, the unique configuration of the guide member 150 relative to the first pedicle screw 12 insures that the second pedicle screw 14 will be properly offset and aligned with the first pedicle screw 12 in the vertebra 118.

Thus, another advantage of the guide member 150 of the present disclosure is that the coupling portion 152 of the guide member 150 is operable to couple with the coupling portion 100 of the first pedicle screw 12 such that the offset member 154 extends in a predetermined direction relative to the coupling of the coupling portion 152 of the guide member 150 to the coupling portion 100 of the first pedicle screw 12. The offset member 154 of the guide member 150 is positionable relative to the coupling of the coupling portion 152 of the guide member 150 with the coupling portion 100 of the first pedicle screw 12.

It will be appreciated that the connection of the coupling portion 152 of the guide member 150 to the coupling portion 100 of the first pedicle screw 12 must be a locking or fitted type connection such that the offset member 154 properly extends in the proper direction to position the alignment member 156 for proper placement of the second pedicle screw 14. Achieving the accuracy necessary to locate the proper placement of the second pedicle screw 14, which will not be visible since the first pedicle screw 12 will be embedded within the vertebra 118, is preferably accomplished through the accurate coupling connection of the coupling portion 152 of the guide member 150 to the coupling portion 100 of the first pedicle screw 12.

It should be understood, however, that a number of other methods of properly aligning the placement of the second pedicle screw 14 may be utilized. For example, one method may include providing indicia or markings on the head 28 of the first pedicle screw 12 indicating the relative position of the first pedicle screw 12. The coupling portion 152 may further include an extension (not shown) extendable through the passageway 110 of the shaft 20 of the first pedicle screw 12. The extension of the coupling portion 152 of the guide member 150 may be similarly provided with indicia, markings, or an alignment with the indicia provided on the head 28 of the first pedicle screw 12. In this manner, when the indicia are aligned, so is the alignment member 156 aligned with the proper placement of the second pedicle screw 14.

A variety of other methods for obtaining this positioning and alignment for aligning the second pedicle screw 14 relative to the first pedicle screw 12 will readily suggest themselves to one of ordinary skill in the art and are within the spirit and scope of the present disclosure and will not be discussed for purposes of brevity.

Figure 7:
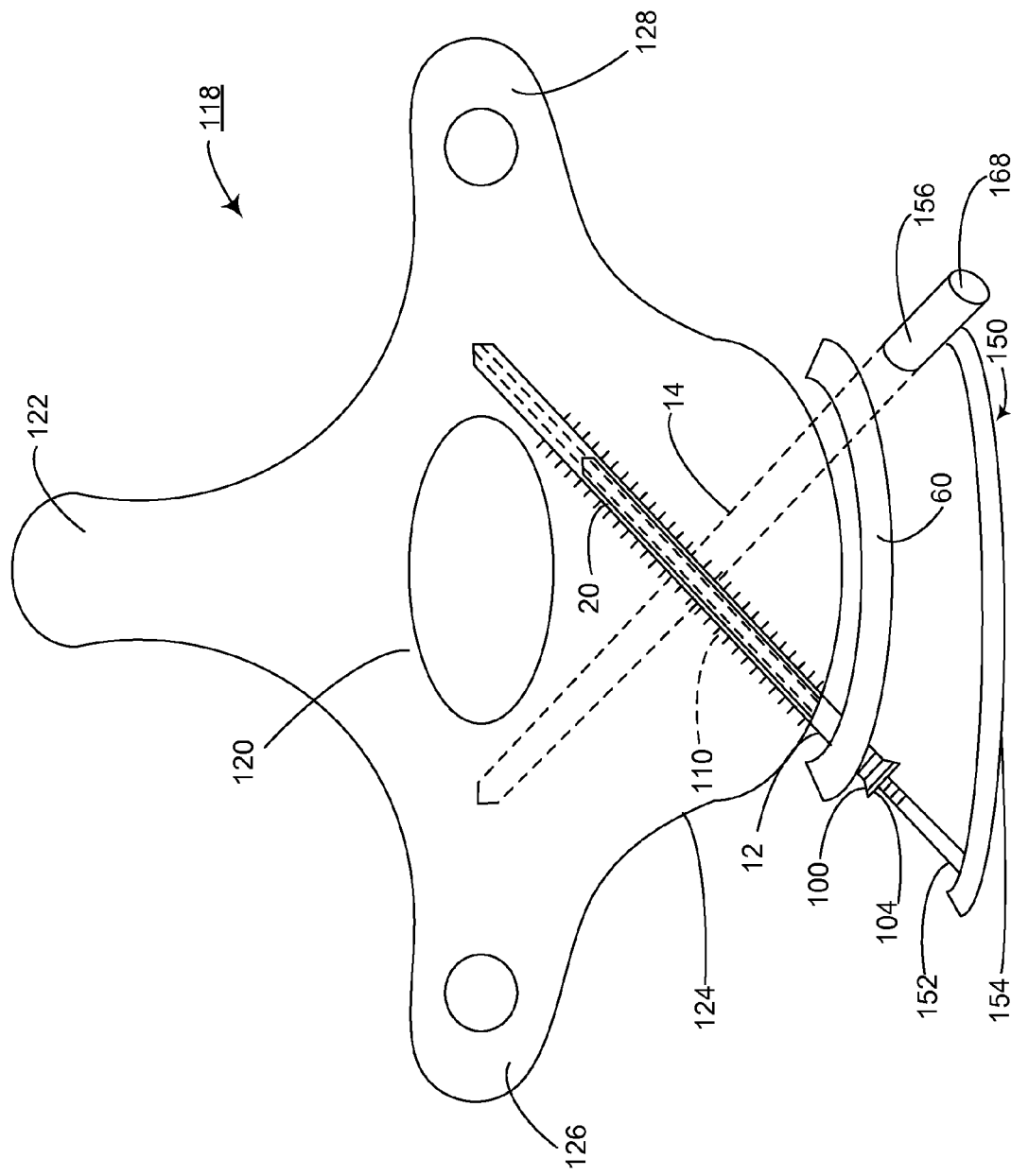
FIG. 7 illustrates a left side anterior positioning of the pedicle screw and alignment of the second pedicle screw utilizing the guide member according to yet another aspect of the present disclosure.

FIG. 7 illustrates an alternative left side 126 placement of the first pedicle screw 12 in the vertebra 118. Procedurally, numerous methods may be utilized to determine whether the first pedicle screw 12 is satisfactorily stabilized within the vertebra 118, including electrical stimulation to test for a desired threshold. In certain circumstances, such as when the right side 128 placement of the first pedicle screw 12 is ineffective to achieve the desired or required stability, left side 126 placement of the first pedicle screw 12 may be necessary. In this instance, the present disclosure may be utilized in substantially the same manner for left side 126 placement.

Figure 8:
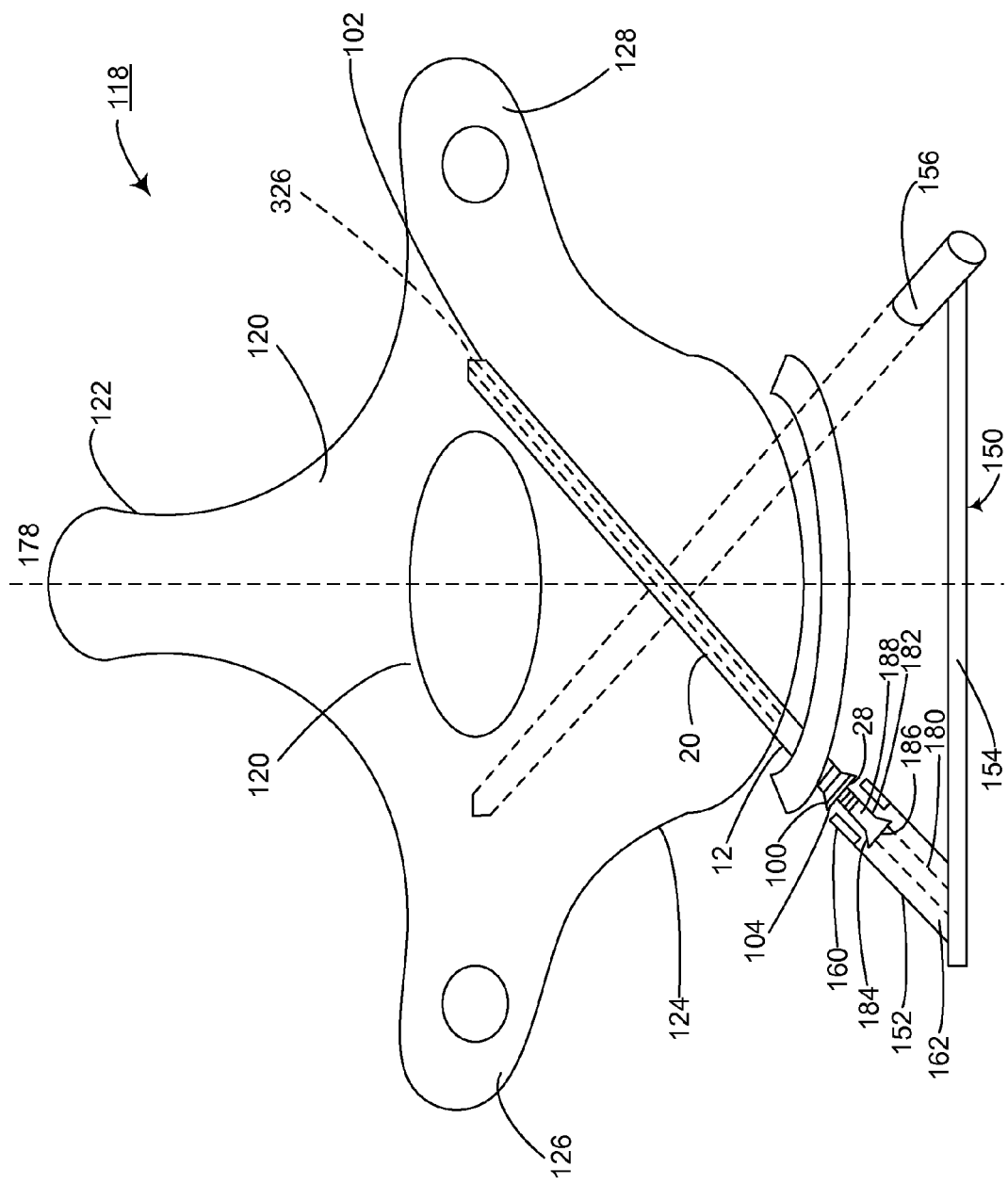
FIG. 8 is a top plan view of other aspects of the guide member and the pedicle screw shown connected in accordance with yet another aspect of the present disclosure.

FIG. 8 illustrates another aspect of the first pedicle screw 12 as well as another aspect of the guide member 150. The vertebra 118 is shown having a midline 178 extending from the anterior side 124 to the posterior side 122 of the vertebra 118. The coupling portion 152 of the guide member 150 is shown connected to the first pedicle screw 12 on the right side 128 of the vertebra 118 adjacent the midline 178. As previously discussed, placement of the first pedicle screw 12 on the right 128 anterior side 124 of the vertebra 118 may be preferable.

In this aspect the guide member 150 is shown having a substantially non-arcuate offset member 154 such that the alignment member 156 extends angularly from the offset member 154. The coupling portion 152 is shown as a substantially tubular member having a channel 180 extending through the coupling portion 152. The coupling portion 152 is provided with a recess 182 extending into the channel 180 near the first end 160 of the coupling portion 152. Furthermore, in this aspect, the first end 160 of the coupling portion 152 is adapted to matingly receive the first pedicle screw 12 near the engaging end 104 thereof. As previously discussed, the first pedicle screw 12 is provided with a coupling portion 100, in this aspect, as an opening in the engaging end 104 of the first pedicle screw 12.

A locking screw 184 may be extended through the channel 180 from the second end 162 toward the first end 160 of the coupling portion 152. The locking screw 184 is provided with a head 186 having a larger diameter than that of a shaft 188 portion of the locking screw 184. The first end 160 of the coupling portion 152 is matingly connectable to the engaging end 104 of the first pedicle screw 12. The locking screw 184 is positioned through the channel 180 until the shaft 188 portion of the locking screw 184 couples with the coupling portion 100 of the first pedicle screw 12.

A tool (not shown) having any standard screw driver or hex, octagonal-type or other connection, for example, may be extended down the channel 180 and used to connect the locking screw 184 to the coupling portion 100 of the first pedicle screw 12. The locking screw 184 may be threadingly screwed into engagement with the first pedicle screw 12 or connected in other manners which are well known and will readily suggest themselves to one of ordinary skill in the art.

In this manner, the head 186 of the locking screw 184 engages the recess 182 within the channel 180 of the coupling portion 152 thereby engaging the coupling portion 152 to the first pedicle screw 12. It will be appreciated that the locking screw 184, the coupling portion 152, and the guide member 150 may be provided with indicia or markings to indicate locking engagement and alignment with both the first pedicle screw 12 and the vertebra 118 since it is critical that the locking screw 184 couple the coupling portion 152 to the first pedicle screw 12 at a particular position relative to the vertebra 118. The indicia or markings may include cross-hair lines, a single line or mark, an arrow, or other markings indicating a rotational position desired for achieving this connection and location.

Such accurate positioning may be accomplished based on the threads of the shaft 188 of the locking screw 184 corresponding to threaded openings within the coupling portion 100 of the first pedicle screw 12. A secure locking connection for alignment of the guide member 150 with the first pedicle screw 12 may be achieved via a variety of different structural attachments. For example, a structure attachment may be such that the alignment member 156 may be engaged to the engaging portion 26 on the shaft 20 of the first pedicle screw 12 and other attachment methods are within the spirit and scope of the present disclosure and will readily suggest themselves to one of ordinary skill in the art.

Also, in one aspect, the procedure for placing the first pedicle screw 12 from the anterior side 124 of the vertebra 118 may include drilling a hole utilizing a drill or other device or implement through the outer surface of the anterior side 124 of the vertebra 118 to penetrate the hard outer bone surface. Thereafter, utilizing technology typically employed for such purposes, such as an image intensifier, x-ray and templates, and/or other stealth technology, a K-wire or other drill or penetrating implement may be utilized to penetrate in a direction toward the posterior side 122 along a line 326. The K-wire may be obliquely placed through the vertebral body into the pedicle 120 on the right side 128. A cannulated drill may be utilized to drill over the K-wire to ream out a hole or opening for placement of the first pedicle screw 12 therein. The drill and K-wire may be removed and the first pedicle screw 12 may be anteriorly placed in the drilled opening substantially along the line 326 for proper placement of the first pedicle screw 12 in the vertebra 118. This aspect, as previously discussed, advantageously provides for selecting, in advance, the proper pedicle screw, such as the first pedicle screw 12, to achieve the desired angle and placement of the first pedicle screw 12.

Another advantage of anterior placement of the first pedicle screw 12 is that it provides the opportunity for stabilization from the posterior side 122 when such may be desirable. In this aspect, the first pedicle screw 12, such as that illustrated and previously disclosed herein in a number of different embodiments, may be utilized by placement initially from the anterior side 124 such that the distal end 102 is anchored substantially in the pedicle 120 portion of the vertebra 118.

Under the preferred anterior stabilization and when the first pedicle screw 12 is placed from the anterior side 124 of the vertebra 118, the first pedicle screw 12 is provided with a coupling portion 100 near the head 28 of the first pedicle screw 12, substantially as shown in FIG. 8.

Utilization of the vertebral stabilization assembly 10 according to the aspect illustrated in FIG. 8, has the additional advantage of completely eliminating rotation of the patient during the procedure. However, it will be appreciated that there may be certain instances when it is necessary or useful to rotate the patient for posterior access to the vertebra 118 and such rotation will not reduce or detract from the advantages of the vertebral stabilization assembly 10 of the present disclosure in that a significant portion or all of the procedure may be achieved from the anterior side 124 of the vertebra 118. This presents a significant advantage in that rotation of the patient takes considerable time and eliminating the necessity for such rotation shortens the time period required for the procedure.

In some instances, anterior placement on the left side may be advantageous. The reason that this placement may be preferable is that the angle of the shaft 20 of the first pedicle screw 12 is shallower with respect to the second pedicle screw 14. This shallower angle will require a smaller guide member 150 and result in the surgery being performed in a smaller physical area. Since space is limited in the cavity of the patient, this configuration may be useful in some circumstances. Also, anterior placement of the pedicle screw on the left side may be utilized as a salvage means when the right side becomes fractured or the desired stabilization is not obtained on the right side of the vertebra 118.

Figure 9:
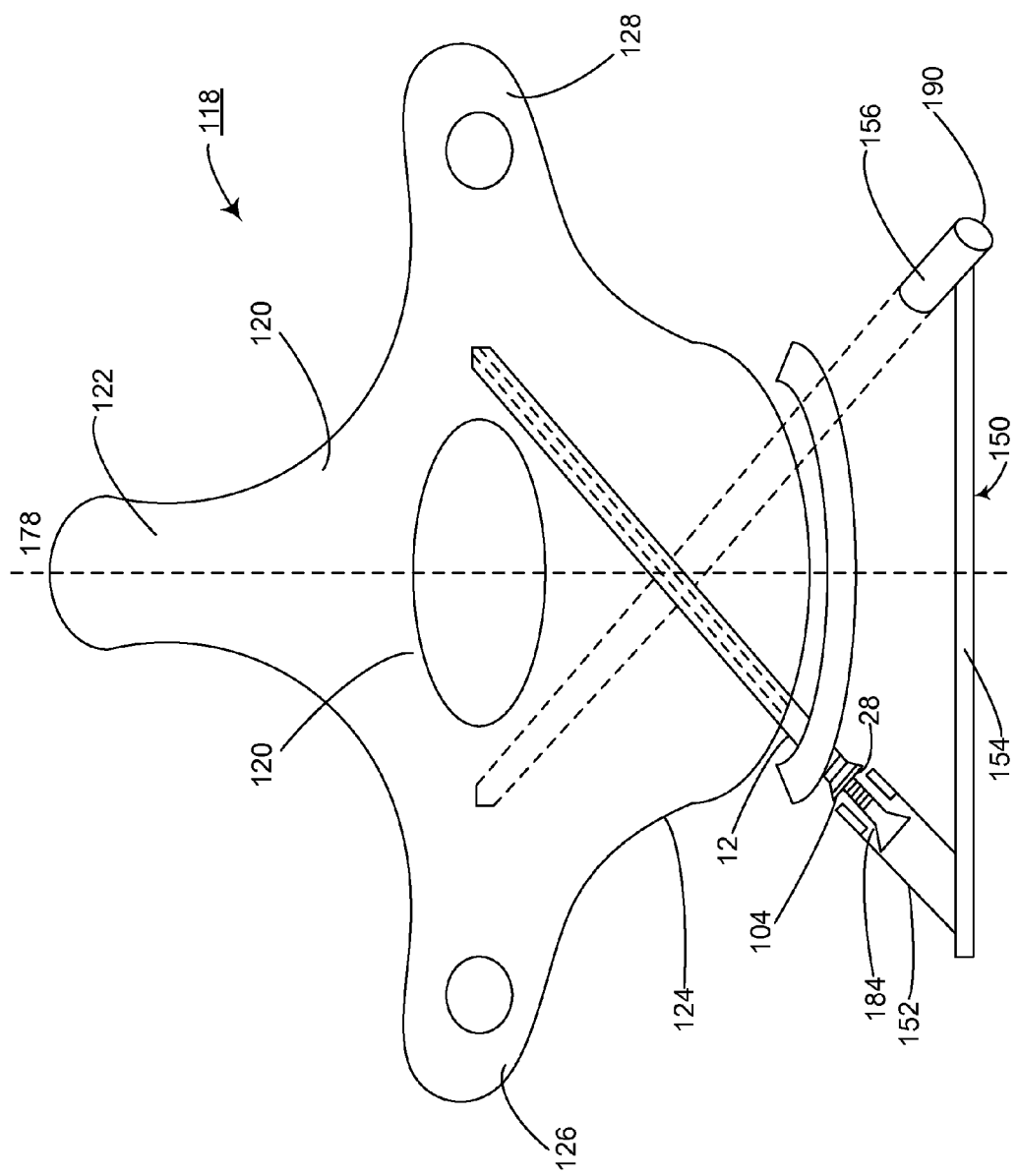
FIG. 9 illustrates alignment of the second pedicle screw utilizing the guide member, as shown in FIG. 8, for attachment of the second pedicle screw positioned within the vertebra according to one aspect of the present disclosure.

FIG. 9 illustrates the first pedicle screw 12 placed from the left side 126 on the anterior side 124 of the vertebra 118. It will be appreciated that the exact placement and size of the first pedicle screw 12 relative to the vertebra 118, as shown and disclosed, herein may be enlarged or reduced proportionately depending upon the characteristics of the vertebra 118 and the goals of the vertebral stabilization assembly 10. However, the first pedicle screw 12 is preferably secured in the pedicle portion 120 of the vertebra 118 such that the engaging end 104 of the first pedicle screw 12 is coupleable to the guide member 150 on the left side 126 on the anterior side 124 adjacent the midline 178 of the vertebra 118.

In some aspects, the guide member 150 may be provided with a rotational coupling 190 such as a recess or opening in the offset member 154 of the guide member 150. The rotational coupling 190 may be adapted as an opening to receive a tool or device for obtaining leverage on the guide member 150 for rotation of the guide member 150. It will be appreciated that while the first pedicle screw 12 may be provided with indicia or other markings on the head 28 of the first pedicle screw 12 for determining the location and disposition of the second pedicle screw 14, a surgeon may have difficulty determining from the anterior side 124 of the vertebra 118 the optimum location for placement of the second pedicle screw 14.

Once the guide member 150 is connected to the first pedicle screw 12 on the anterior side 124 of the vertebra 118, only then will the surgeon be able to determine the preferable placement of the second pedicle screw 14 relative to the first pedicle screw 12 and the body of the vertebra 118. In the event the first pedicle screw 12 is not aligned preferably for the second pedicle screw 14, by use of the rotational coupling 190, such as with a tool connected thereto, the surgeon may rotate the guide member 150 and the first pedicle screw 12 rigidly connected thereto, via the locking screw 184, to obtain the optimum placement of the second pedicle screw 14 into a desired point in the body of the vertebra 118. In other embodiments, the guide member 150 may not include the rotational coupling 190 and, as such, this rotational alignment may be achieved by grasping and rotating the offset member 154 or other portions of the guide member 150.

Once this optimum positioning has been obtained by rotation using the rotational coupling 190 the tool coupled to the rotational coupling 190 may be removed and a drill or other tool may be utilized and aligned via the alignment member 156 for drilling an opening into the body of the vertebra 118 at the desired location. Thereafter, the second pedicle screw 14 may be properly placed into the body of the vertebra 118 at the desired location.

It will be appreciated that the locking screw 184 may be connected in a variety of manners to the coupling portion 152 of the guide member 150 to obtain a corresponding rotation of the guide member 150 with the first pedicle screw 12 for these rotational purposes which will readily suggest themselves to one of ordinary skill in the art and are within the spirit and scope of the present disclosure.

Figure 10:
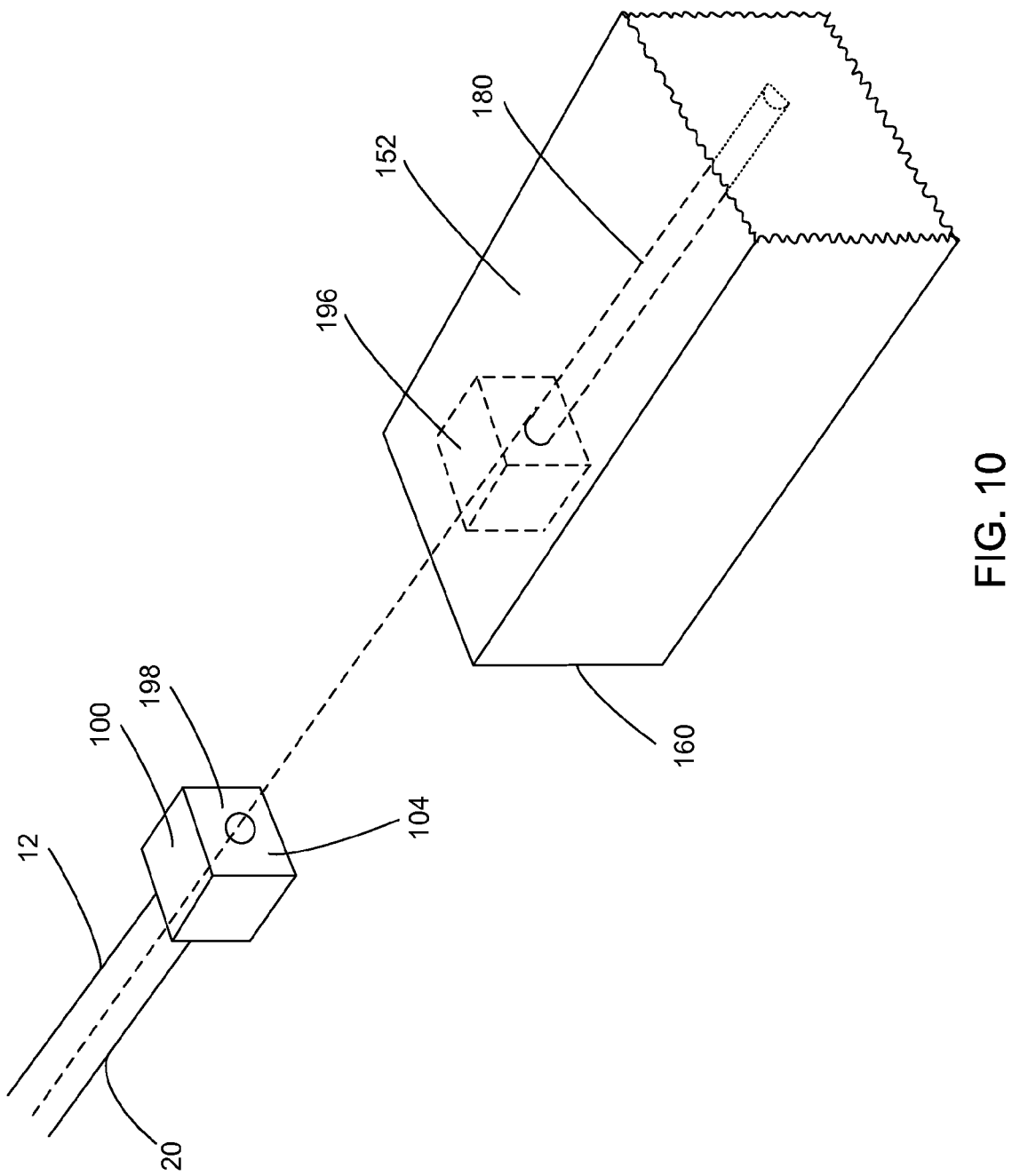
FIG. 10 is a perspective view illustrating yet another aspect of the connection of the pedicle screw with the guide member constructed in accordance with an embodiment of the present disclosure.

FIG. 10 illustrates another aspect of the connection of the first pedicle screw 12 to the coupling portion 152 of the guide member 150. As previously discussed above, a variety of methods exist for connecting the coupling portion 152 with the coupling portion 100 of the first pedicle screw 12. In the present aspect illustrated in FIG. 10, the coupling portion 100 of the first pedicle screw 12 is a substantially rectangular member extending from the shaft 20 of the first pedicle screw 12.

The coupling portion 152 of the guide member 150, in the present aspect, is provided with a substantially rectangular opening 196 in the first end 160 of the coupling portion 152. The substantially rectangular opening 196 is sized to matingly receive the rectangular coupling portion 100 to achieve a fitted coupling there between. In this aspect, the coupling portion 100 may be provided with a threaded opening 198 on the engaging end 104 of the first pedicle screw 12. In this manner, the channel 180 extending through the coupling portion 152 may be provided to guide a connecting member, such as the locking screw 184 or other engaging structure, to be threadingly received by the threaded opening 198 in the engaging end 104 of the first pedicle screw 12.

In this manner, the combination of the locking mechanism, such as the locking screw 184, as well as the rectangular configuration of the coupling portion 100 of the first pedicle screw 12 with the substantially rectangular opening 196 in the first end 160 of the coupling portion 152, promotes an accurately engaged connection of the guide member 150 with the first pedicle screw 12. It should be appreciated that in other aspects the threaded opening 198 and the channel 180 may be eliminated and only the mating connection of the rectangular coupling portion 100 of the first pedicle screw 12 with the substantially rectangular opening 196 of the coupling portion 152 will be sufficient for this connection.

It will be appreciated that the configuration illustrated in the current aspect promotes a sufficient engagement of the guide member 150 to the first pedicle screw 12 to achieve engaging rotation of the first pedicle screw 12 by the guide member 150 when such adjustment for alignment purposes of the first pedicle screw 12 is desirous. It should be appreciated that while the coupling portion 100 of the current aspect is shown as substantially rectangular in configuration as is the substantially rectangular opening 196 of the coupling portion 152 of the guide member 150, a variety of other configurations such as, but not limited to, triangular configurations, will readily suggest themselves to one of ordinary skill in the art and are within the spirit and scope of the present disclosure, as are a variety of other coupling connections between the coupling portion 152 and the first pedicle screw 12 which may be utilized to achieve these purposes.

Figure 11:
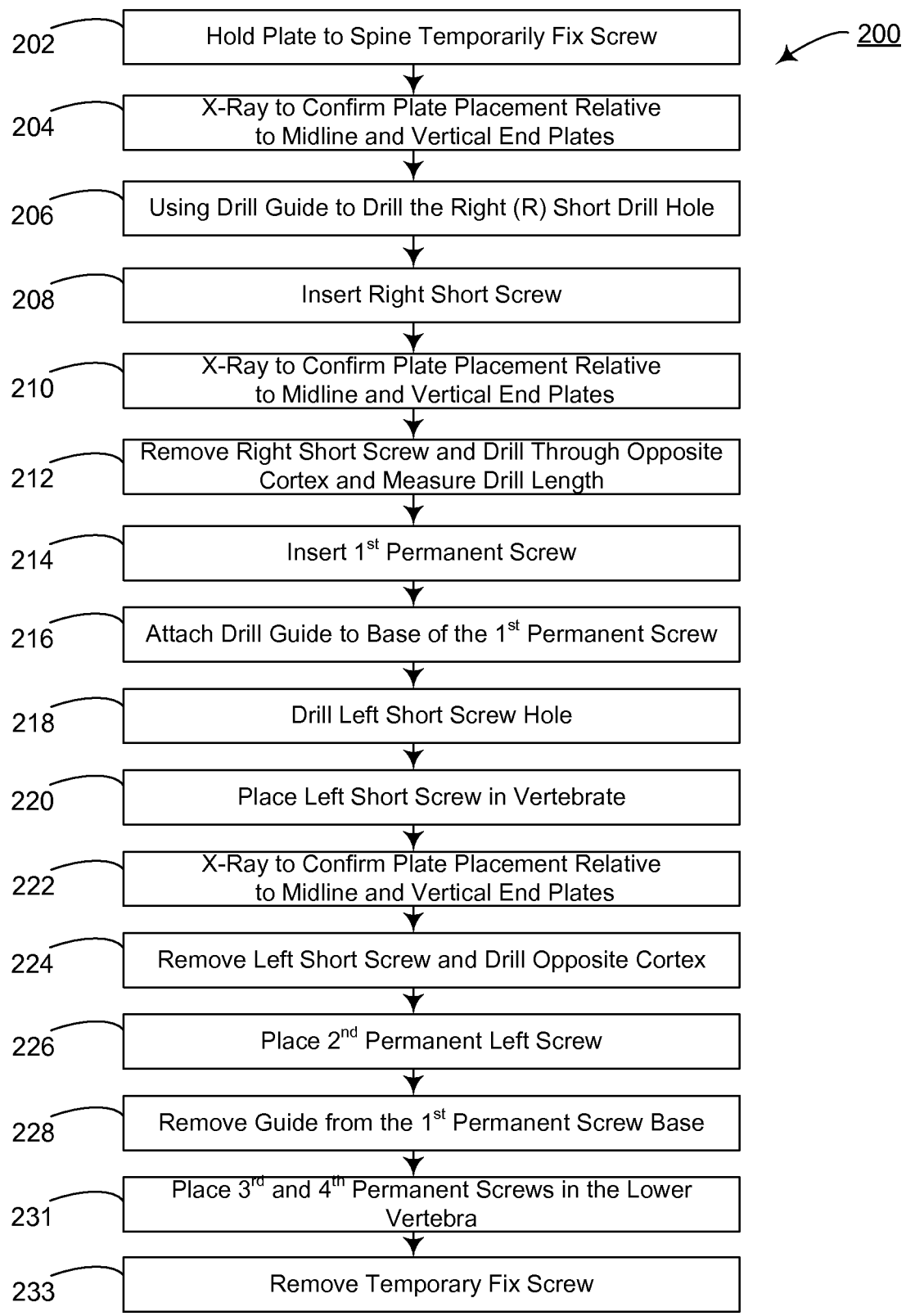
FIG. 11 is a flow chart illustrating a method for stabilizing vertebrae from the utilizing the vertebral screw arrangement with locking pin of the present disclosure.

FIG. 11 is a flow chart illustrating a method 1100 for stabilizing an upper and lower vertebra 118A and 118B, substantially similar to the vertebra 118 illustrated in FIGS. 4 and 6-9, from an anterior side 124 of the vertebrae 118A and 118B using the vertebral stabilization assembly 10 in accordance with the present disclosure. The method includes, at a block 202, temporarily fixing a connecting member 60 in a desired position to the upper and lower vertebrae 118A and 118B. The connecting member 60 may include a plurality temporary fixing holes for engaging a temporary fixing screw. In other aspects, the temporary fixing holes may include a threading or tensioning or locking connection. Also, in other aspects, the connecting member 60 may temporarily fixed to the upper and lower vertebrae 118A and 118B by a welded or bonded connection. Although welding or bonding engagements may be used to temporarily fix the connecting member 60 to the upper and lower vertebrae 118A and 118B, it should be appreciated that bonding or other gluing or tacking materials may be used for this connection and satisfactory for these purposes.

At block 204, x-ray, stealth, or other imaging technologies may be employed to ensure the accurate alignment and placement of the connecting member 60 relative to the midline 178 of the upper and lower vertebrae 118A and 118B and top end of upper vertebra 118A and lower end of lower vertebra 118B.

At block 206, K-wire or other drill or penetrating implement may be utilized to penetrate obliquely from the anterior side 124 of vertebra 118A in a direction toward the posterior side 122 along a predetermined line. The drilling may only penetrate a short distance into the body of the vertebra 118A in which the drilling may fail to extend into the cortex area of the pedicle 120 of the vertebra 118A.

At block 208, a cannulated drill may be utilized to drill over the K-wire to ream out a hole or opening for placement of a short screw with substantially the same construction as the first pedicle screw 12 therein. The drill and K-wire may be removed and the short screw may be anteriorly placed in the drilled opening substantially along the predetermined line.

At block 210, x-ray, stealth, or other imaging technologies may be employed to ensure the accurate alignment and placement of the short screw relative to the predetermined line before the drilling extends to the cortex area of the pedicle 120 of the vertebra 118A. This aspect advantageously ensures proper alignment of the drilling path and adjustments may be made before drilling to the cortex area of the pedicle 120 of the vertebra 118A.

At block 212, the short screw may be removed and the K-wire or other drill or penetrating implement may be utilized to continue to penetrate obliquely through the opposite cortex area of the pedicle 120 of the vertebra 118A. Also, the drill length may be measured in order prevent damages caused to the patient by over drilling. A cannulated drill may be utilized to drill over the K-wire to ream out a hole or opening for placement of the first pedicle screw 12 therein.

At block 214, the drill and K-wire may be removed and the first pedicle screw 12 may be anteriorly placed in the drilled opening substantially along the predetermined line to the opposite cortex area of the pedicle 120 for proper placement of the first pedicle screw 12 in the vertebra 118A.

At a block 216 the guide member 150 may be coupled to the coupling portion 100 of the shaft 20 of the first pedicle screw 12 from the anterior side 124 of the vertebra 118A. In one aspect, the coupling of the guide member 150 may be more readily accomplished after an opening has been drilled through the anterior side 124 of the vertebra 118.

At block 218, the K-wire or other drill or penetrating implement may be utilized to penetrate obliquely from the left side 126 of the anterior side 124 of the vertebra 118A in a direction toward the right side 128 of the posterior side 122 along a predetermined line. The drilling only penetrates a short distance into the body of the vertebra 118A in which the drilling fails to extend to the cortex area of the pedicle 120 of the vertebra 118A.

At block 220, a cannulated drill may be utilized to drill over the K-wire to ream out a hole or opening for the placement of a short screw with substantially the same construction as the second pedicle screw 14 therein. The drill and K-wire may be removed and the short screw may be anteriorly placed in the drilled opening substantially along the predetermined line.

At block 222, x-ray, stealth, MRI or other imaging technologies may be employed to ensure the accurate alignment and placement of the short screw relative to the predetermined line before the drilling extends to the cortex area of the pedicle 120 of the vertebra 118A. This aspect advantageously ensures proper alignment of the drilling path and adjustments may be made before drilling to the cortex area of the pedicle 120 of the vertebra 118A.

At block 224, the short screw may be removed and the K-wire or other drill or penetrating implement may be utilized to continue to penetrate obliquely through the opposite cortex area of the pedicle 120 of the vertebra 118A. Also, the drill length may be measured in order prevent damages caused to the patient by over drilling. A cannulated drill may be utilized to drill over the K-wire to ream out a hole or opening for placement of the second pedicle screw 14 therein.

At block 226, the drill and K-wire may be removed and the second pedicle screw 14 may be anteriorly placed in the drilled opening substantially along the predetermined line to the opposite cortex area of the pedicle 120 for proper placement of the second pedicle screw 12 in the vertebra 118A.

At block 228, guide member 150 may be removed from the first pedicle screw 12.

Subsequently at block 231, the third and fourth pedicle screws 16 and 18 may be placed into the lower vertebra 118B according to the method described above. Thus, the vertebral stabilization assembly 10 may support the upper and lower vertebra 118A and 118B. At block 233, the temporarily fixing means may be removed.

Figure 12:
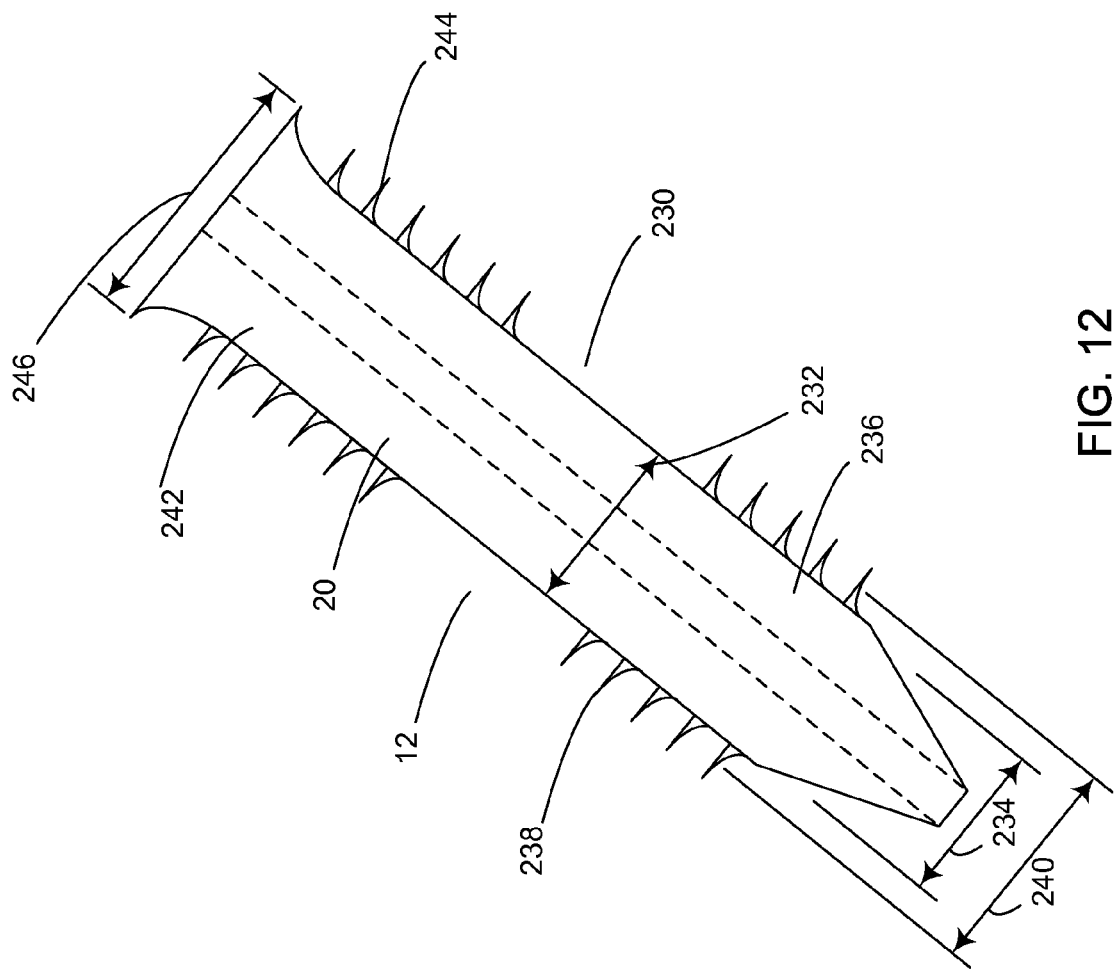
FIG. 12 is a perspective view illustrating yet another aspect of the pedicle screw provided with a shaft having a reinforced portion.

FIG. 12 illustrates another aspect of the first pedicle screw 12 having a reinforced portion 230 provided on the shaft 20. The reinforced portion 230 of the shaft 20 provides additional structural support for fixating the vertebra 118 in place. The reinforced portion 230 is shown having a diameter 232 that is greater than a diameter 234 of a first threaded portion 236 of the shaft 20. In this manner, it is readily apparent that the reinforced portion 230 having a greater diameter 232 will provide additional structural support of the vertebra 118 with respect to the smaller diameter 234 of the first threaded portion 236 of the shaft 20. The first threaded portion 236 of the shaft 20 is provided with a plurality of threads 238 connected to and extending from the shaft 20 of the first pedicle screw 12. It can be seen that the diameter 232 of the reinforced portion 230 is about equal to a diameter 240 measured from an outermost edge of the plurality of threads 238 of the first threaded portion 236.

As the first pedicle screw 12 is threadingly engaged into the pedicle portion 120 of the vertebra 118, such as the first vertebrae 24, the first threaded portion 236 will threadingly engage and retain the first pedicle screw 12 within the first vertebrae 24. In the present embodiment the reinforced portion 230 is not provided with threads, however, in other embodiments the reinforced portion may be provided with threads similar to the plurality of threads 238 or threads extending less far from the reinforced portion 230 than the plurality of threads 238 extend from the first threaded portion 236 of the shaft 20. In one aspect, the diameter 232 of the reinforced portion 230 is about 6.5 millimeters. However, in other embodiments the diameter 232 of the reinforced portion 230 may be greater or less than 6.5 millimeters as may be necessary to properly engage the shaft 20 of the first pedicle screw 12 in the first vertebrae 24.

The shaft 20 of the first pedicle screw 12 is further provided with a second threaded portion 242 having a plurality of threads 244 for engaging the first vertebrae 24. In the present aspect, the diameter 232 of the reinforced portion 230 is less than a diameter 246 measured from an outermost edge of the plurality of threads 244 provided on the second threaded portion 242. As the first pedicle screw 12, of the present aspect, is engaged into the first vertebrae 24, the first threaded portion 236 will threadingly engage an interior vertebral body portion and thereafter the pedicle portion 120 of the first vertebrae 24. As the reinforced portion 230 of the first pedicle screw 12 follows behind the first threaded portion 236, the reinforced portion 230 may have the affect of smoothing the threading engagement within the vertebral body. For this reason, it may be advantageous to provide the plurality of threads 244 having a greater diameter 246 for providing additional threading engagement of the first pedicle screw 12. In other aspects (not shown), frictional engaging surface structure, such as small or low profile threads, may be provided on the reinforced portion 230 for frictionally engaging the inner vertebral body at the first vertebrae 24.

In the present aspect, the diameter 246 of the plurality of threads 244 may be about 7.0 millimeters to achieve additional threading engagement of the second threaded portion 242 of the shaft 20 for stable engagement of the first pedicle screw 12 within the first vertebrae 24. It will be appreciated, however, that in other aspects (not shown) the diameter 246 of the plurality of threads 244 may be of larger or smaller diameter or may be of a similar or smaller diameter than the diameter 232 of the reinforced portion 230 and be adequate for these purposes. Furthermore, in other aspects (not shown) the diameter 234 of the first threaded portion 236 of the shaft 20 may be the same or larger diameter than that of the diameter 232 of the reinforced portion 230. The reinforced portion 230 of the shaft 20 provides significant additional structural support for stabilizing the first vertebrae 24. While the length of the reinforced portion 230 relative to the length of the entire shaft 20 of the first pedicle screw 12 is shown in relative proportion according to the present aspect, the reinforced portion 230, according to other aspects (not shown), may be of significantly greater length and diameter or having a smaller length and diameter relative to the shaft 20 of the first pedicle screw 12 and are within the spirit and scope of the present disclosure as described herein.

Figure 13:
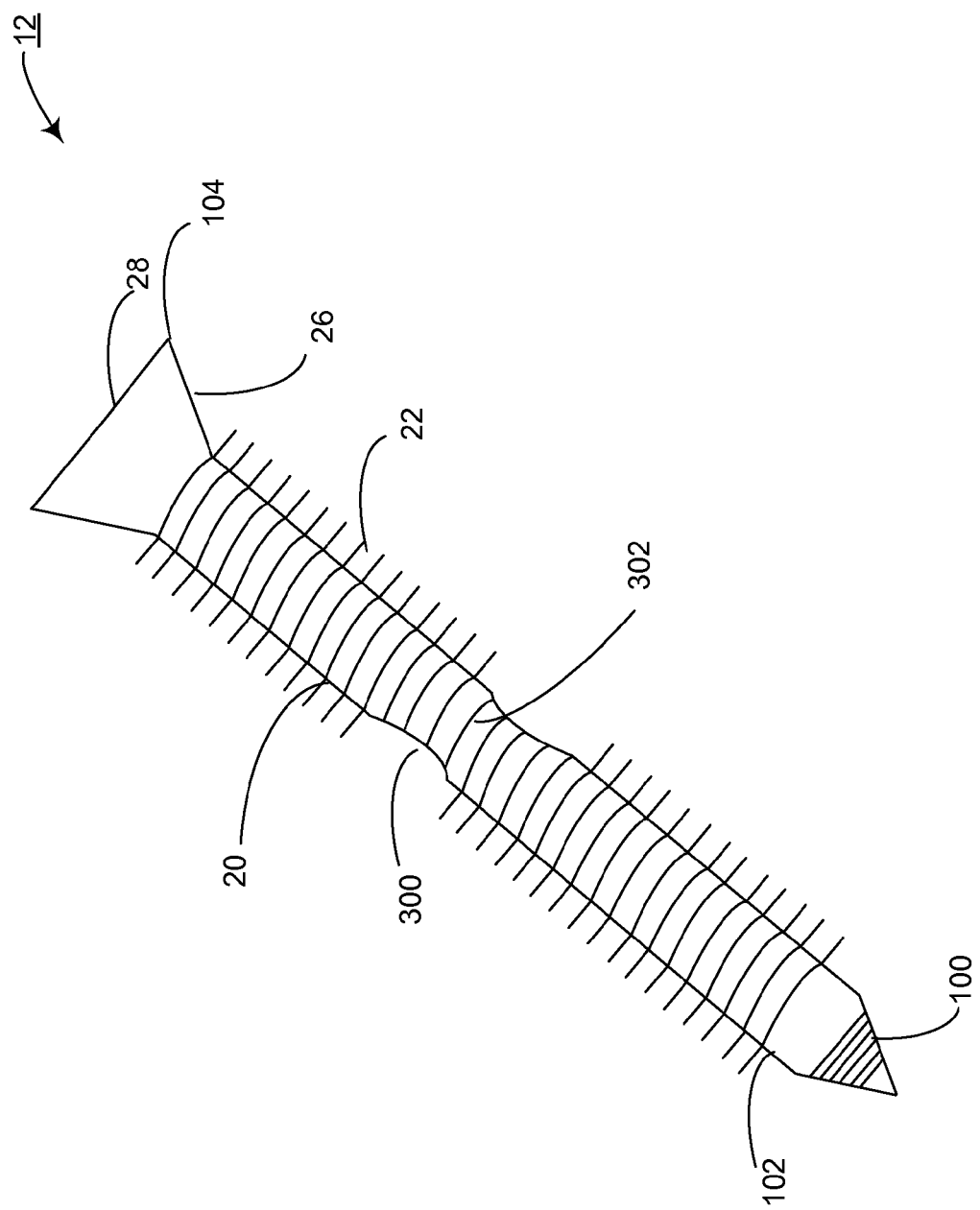
FIG. 13 is a side elevational view of a first pedicle screw according to one alternative aspect of the present disclosure.

FIG. 13 illustrates yet another aspect of a pedicle screw, such as the first pedicle screw 12 of the vertebral stabilization assembly 10, in accordance with an embodiment of the present disclosure. In this aspect, the first pedicle screw 12, as well as having the shaft 20 having the threaded portion 22 and the engaging portion 26, as previously discussed, further includes a coupling portion 100 provided on both ends of the shaft 20. The first pedicle screw 12 also contains transverse channel 300.

The coupling portion 100 is adapted to engage a guide member (discussed in greater detail with reference to FIG. 5) of the vertebral stabilization assembly. In one aspect, the coupling portion 100 may be a threaded portion on the outer surface of the shaft 20 near the distal end 102 of the shaft 20. In another aspect (not shown), the coupling portion 100 may be a threaded portion on the inner surface of the shaft 20 near an engaging end 104 of the shaft 20. The guide member may be threadingly engaged with the coupling portion 100 about the distal end 102 and/or the engaging end 104 of the shaft 20. In other embodiments, however, the coupling portion 100 may be an opening provided in the distal end 102 and/or engaging end 104 of the shaft 20 such that a portion of the guide member may be threadingly received within the opening in the distal end 102 and/or engaging end 104 of the shaft 20 for threading engagement therewith the coupling portion 100.

As previously mentioned, the engaging portion 26 of shaft 20 is operable to engage the connecting member 60. As previously discussed, this rigid engagement may be provided in a variety of manners, such as, but not limited to, a locking engagement, a threading engagement, and a tensioning or other rigid coupling connection of the connecting member 60 with the first pedicle screw 12 about the engaging portion 26.

The transverse channel 300 in the first pedicle screw 12 is a hole located approximately halfway along the length of the first pedicle screw 12 that passes completely through the first pedicle screw 12. The transverse channel 300 thus forms a hollow channel extending completely through the diameter of the first pedicle screw 12. The first pedicle screw 12 retains its structural integrity through sides 302 and 304 (see FIG. 14) along the length of the first pedicle screw 12. The threaded portion 22 extends along the sides 302 and 304 (see FIG. 14) of the first pedicle screw 12. The transverse channel 300 is large enough to allow for the passage and the positioning of another screw, e.g., the second pedicle screw 14, through the transverse channel 300 of the first pedicle screw 12. The transverse channel 300 is also small enough to allow the first pedicle screw 12 to retain its structural integrity via sides 302 and 304. In FIG. 13, the transverse channel 300 is oriented so that it passes through the "sides" of pedicle screw 12 near sides 302 and 304, which comprise the "top" and "bottom" sides of the screw, respectively. The transverse channel 300 may form a channel at an angle less than ninety degrees (acute angle), so that the top and bottom openings of the channel are offset from each other along a transverse axis of the screw. In this embodiment, second pedicle screw 14 and first pedicle screw 12 would cross at an angle less than ninety degrees between the heads of each screw. In another embodiment, the transverse channel 300 may form a channel in the first pedicle screw 12 at a ninety degree angle (right angle), so that the top and bottom openings of the channel are aligned at the same points along a transverse axis of the screw. In this embodiment, second pedicle screw 14 and first pedicle screw 12 would cross at an angle of ninety degrees between the heads of each screw.

Figure 14:
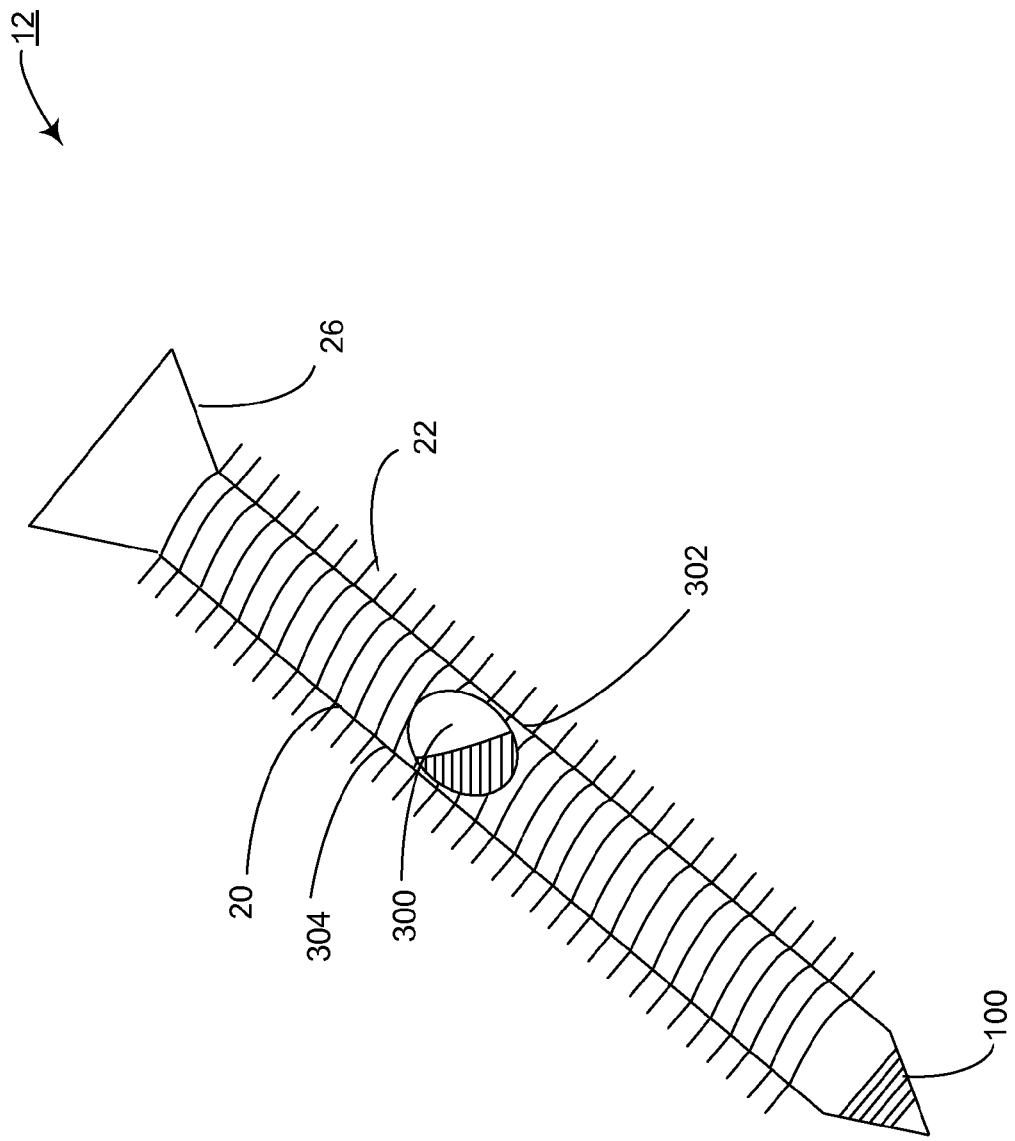
FIG. 14 is a rotated side elevational view of the first pedicle screw according to another alternative aspect of the present disclosure.

FIG. 14 illustrates another aspect of the present disclosure of a pedicle screw, such as the first pedicle screw 12 of the vertebral stabilization assembly 10, in accordance with an embodiment of the present disclosure. In this aspect, the first pedicle screw 12, as well as having the shaft 20 having the threaded portion 22 and the engaging portion 26, as previously discussed, further includes the coupling portion 100 provided on both ends of the shaft 20 and the transverse channel 300. FIG. 14 presents the first pedicle screw 12 of FIG. 13 rotated clockwise by ninety degrees.

The transverse channel 300 is an hole located approximately halfway along the length of the first pedicle screw 12 that passes completely through the first pedicle screw 12. The transverse channel 300 thus forms a hollow channel extending completely through the diameter of the first pedicle screw 12. The first pedicle screw 12 retains its structural integrity via sides 302 and 304 along the length of the first pedicle screw 12. The threaded portion 22 extends along the sides 302 and 304 of the first pedicle screw 12 that define the transverse channel 300. The transverse channel 300 is large enough to allow for the passage and the positioning of another screw, e.g., the second pedicle screw 14, through the transverse channel 300 of the first pedicle screw 12. The transverse channel 300 is also small enough to allow the first pedicle screw 12 to retain its structural integrity via sides 302 and 304. In FIG. 14, the transverse channel 300 is oriented so that it passes through the "sides" of pedicle screw 12 near sides 302 and 304, which comprise the "top" and "bottom" of pedicle screw 12.

Figure 15:
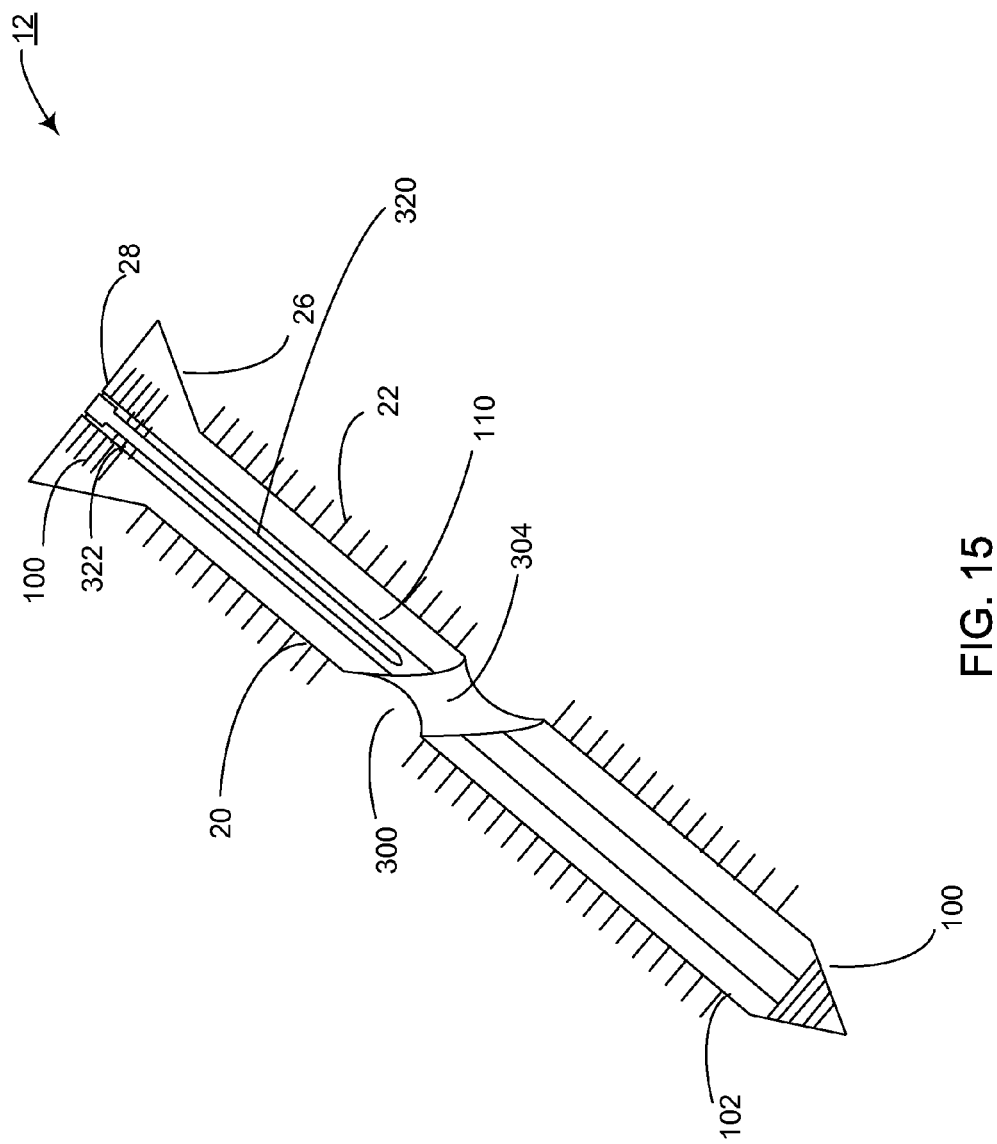
FIG. 15 is a perspective view of the first pedicle screw according to yet another alternative aspect of the present disclosure.

FIG. 15 illustrates another aspect of the present disclosure of a pedicle screw, such as the first pedicle screw 12 of the vertebral stabilization assembly 10, in accordance with an embodiment of the present disclosure. In this aspect, the first pedicle screw 12, as well as having the shaft 20 having the threaded portion 22 and the engaging portion 26, as previously discussed, further includes the coupling portion 100 provided on both ends of the shaft 20 and the transverse channel 300. The first pedicle screw 12 may further comprise a cannulated shaft 20 such that a passageway 110 extends through the shaft 20 from the head 28 to the transverse channel 300, and from the transverse channel 300 to the distal end 102 of the shaft 20.

FIG. 15 presents a cross section of the first pedicle screw 12 of FIG. 13. In this cross-sectional view, the upper and lower portions of pedicle screw 12 appear connected only by side 304, which is located opposite side 302 (not shown in this view). The pedicle screw 12 retains its structural integrity via sides 302 (not shown) and 304. The passageway 110 extends from the head 28 of the shaft 20 to the top edge of the transverse channel 300. The passageway 110 further extends from the bottom edge of the transverse channel 300 to the distal end 102 of the shaft 20. The first pedicle screw 12 is further shown with a locking pin 320, which is secured in place by threads 322 that engage threads of the passageway 110.

Figure 16:
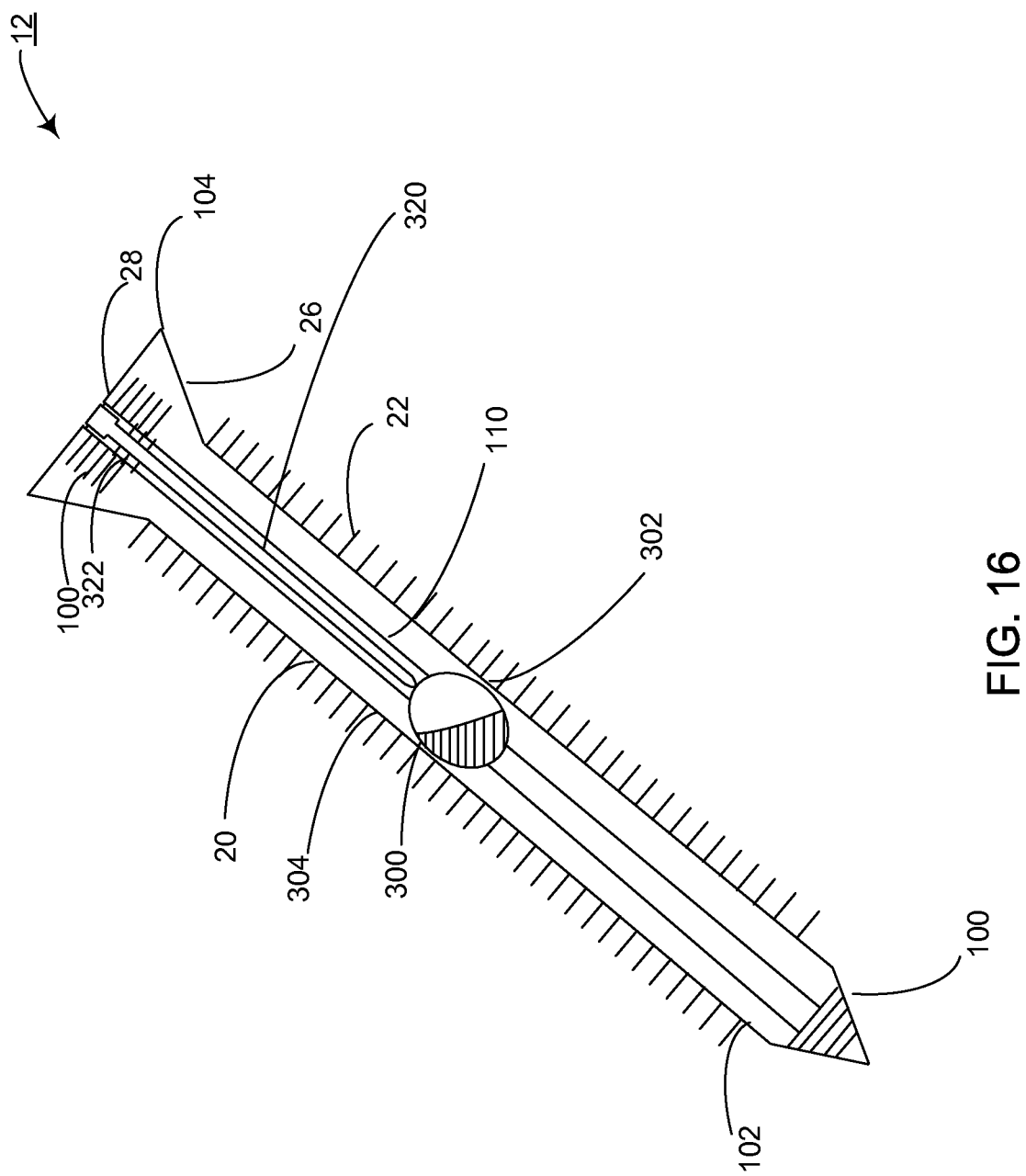
FIG. 16 is a rotated perspective view of the first pedicle screw according to yet another alternative aspect of the present disclosure.

FIG. 16 illustrates another aspect of the present disclosure of a pedicle screw, such as the first pedicle screw 12 of the vertebral stabilization assembly 10, in accordance with an embodiment of the present disclosure. In this aspect, the first pedicle screw 12, as well as having the shaft 20 having the threaded portion 22 and the engaging portion 26, as previously discussed, further includes the coupling portion 100 provided on both ends of the shaft 20 and the transverse channel 300. The first pedicle screw 12 may comprise the cannulated shaft 20 such that the passageway 110 extends through the shaft 20 from the head 28 of the shaft 20 to the transverse channel 300, and from the transverse channel 300 to the distal end 102 of the shaft 20.

FIG. 16 presents a cross section of the first pedicle screw 12 of FIG. 15 rotated clockwise by ninety degrees. In this cross-sectional view, the upper and lower portions of the first pedicle screw 12 appear connected by side 302 and 304. The first pedicle screw 12 retains its structural integrity via sides 302 and 304. The passageway 110 extends from the head 28 of the shaft 20 to the top edge of the transverse channel 300. The passageway 110 further extends from the bottom edge of the transverse channel 300 to the distal end 102 of the shaft 20. The first pedicle screw 12 is further shown with the locking pin 320, which is secured in place by threads 322 that engage threads of the passageway 110.

Figure 17:
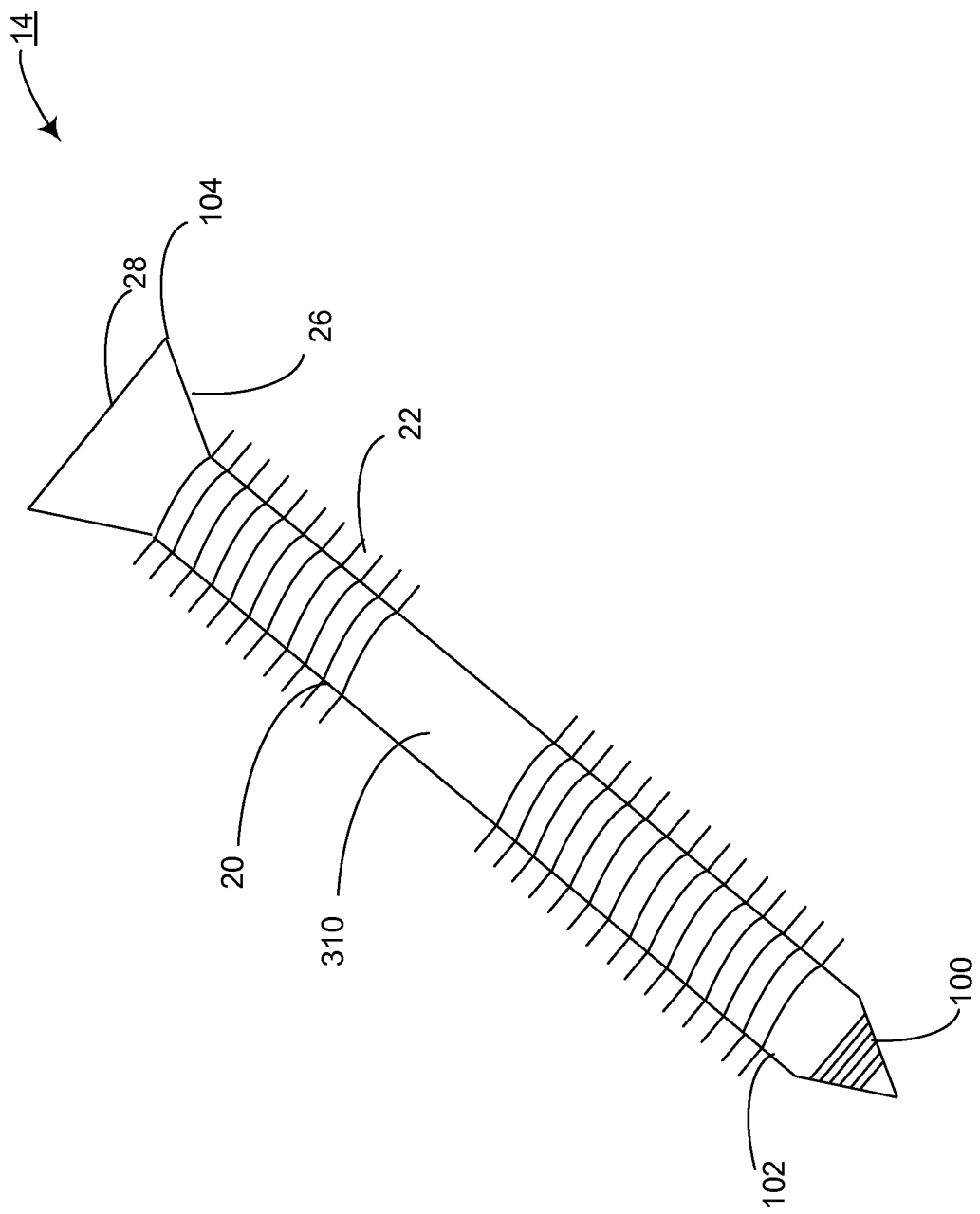
FIG. 17 is a side elevational view of a second pedicle screw according to one alternative aspect of the present disclosure.

FIG. 17 illustrates another aspect of the present disclosure of a pedicle screw, such as the second pedicle screw 14 of the vertebral stabilization assembly 10, in accordance with an embodiment of the present disclosure. In this aspect, the second pedicle screw 14, as well as having the shaft 20 having the threaded portion 22 and the engaging portion 26, further includes a coupling portion 100 provided on both ends of the shaft 20. The second pedicle screw 14 also contains a non-threaded portion 310 located approximately halfway along the length of the second pedicle screw 14. The non-threaded portion 310 is a portion of the second pedicle screw 14 where outside threading is not present, creating a central outside portion that is substantially smooth and unvarying in elevation. The non-threaded portion 310 is optimized to allow the second pedicle screw 14 to pass through another screw, e.g., the first pedicle screw 12, and to allow the second pedicle screw 14 to be secured to the first pedicle screw 12 where they cross such that the threaded portions of the second pedicle screw 14 are adjacent to the outside of the first pedicle screw 12.

Figure 18:
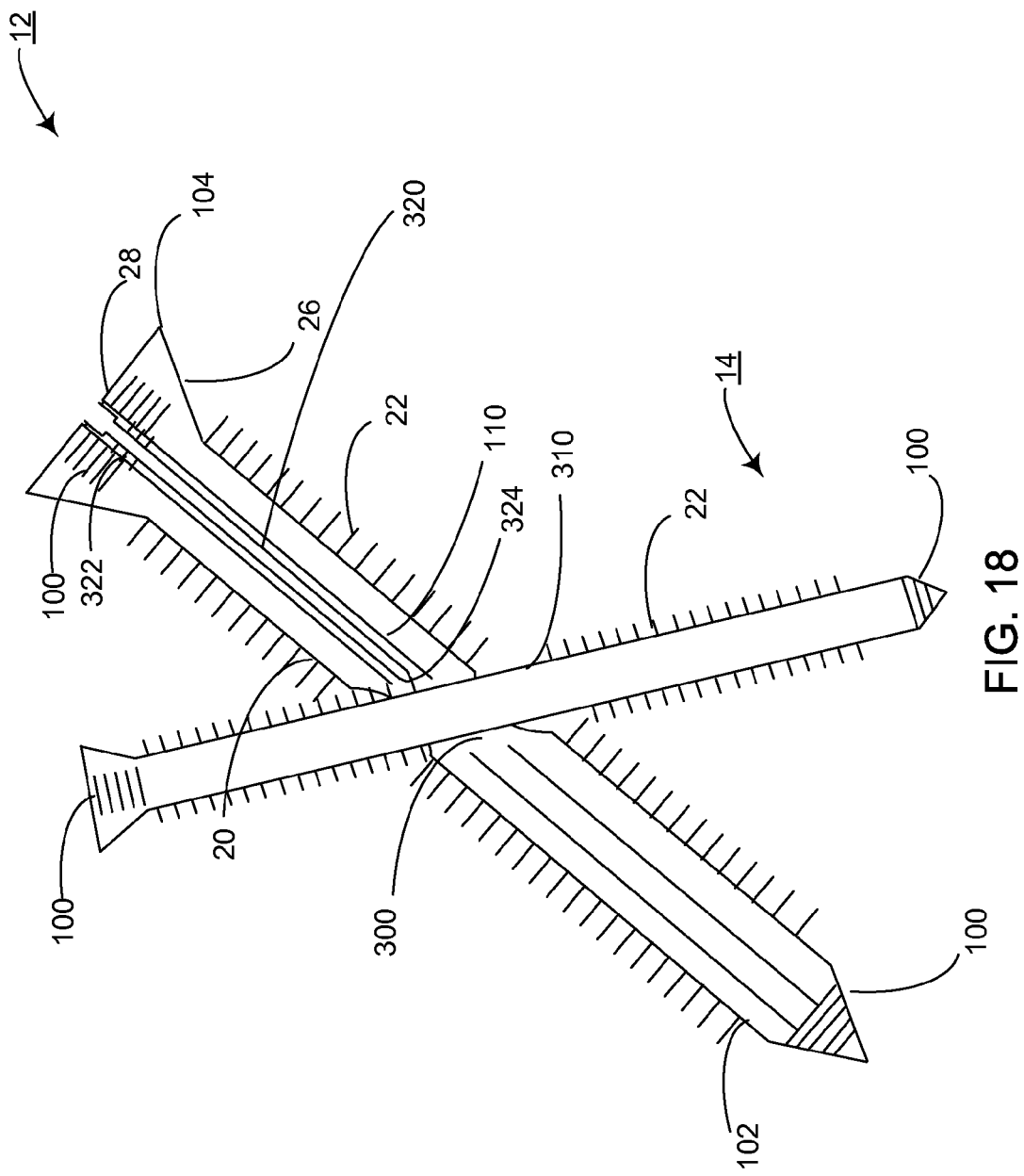
FIG. 18 is a perspective view of the first pedicle screw and the second pedicle screw according to yet another alternative aspect of the present disclosure.

FIG. 18 illustrates yet another aspect of the present disclosure of two pedicle screws, such as the first and second pedicle screws 12 and 14 of the vertebral stabilization assembly 10, in accordance with an embodiment of the present disclosure. In this aspect, the first and second pedicle screws 12 and 14, respectively, contain the transverse channel 300 and the non-threaded portion 310. The first pedicle screw 12 may comprise the cannulated shaft 20 such that the passageway 110 extends through the shaft 20 from the head 28 to the transverse channel 300, and from the transverse channel 300 to the distal end 102 of the shaft 20. First and second pedicle screws 12 and 14 are further shown in a crossing position and are locked in place by a locking pin 320.

To achieve the configuration of FIG. 18, the second pedicle screw 14 of FIG. 17 is placed through the transverse channel 300 of the first pedicle screw 12 of FIGS. 13-16. Once the first and second pedicle screws 12 and 14 are in position, the locking pin 320 may be placed through the passageway 110 until it contacts a thread of the threaded portion 22 or the smooth non-threaded portion 310 of the second pedicle screw 14. The locking pin 320 is secured in place by the threads 322 that engage threads of the passageway 110.

Figure 19:
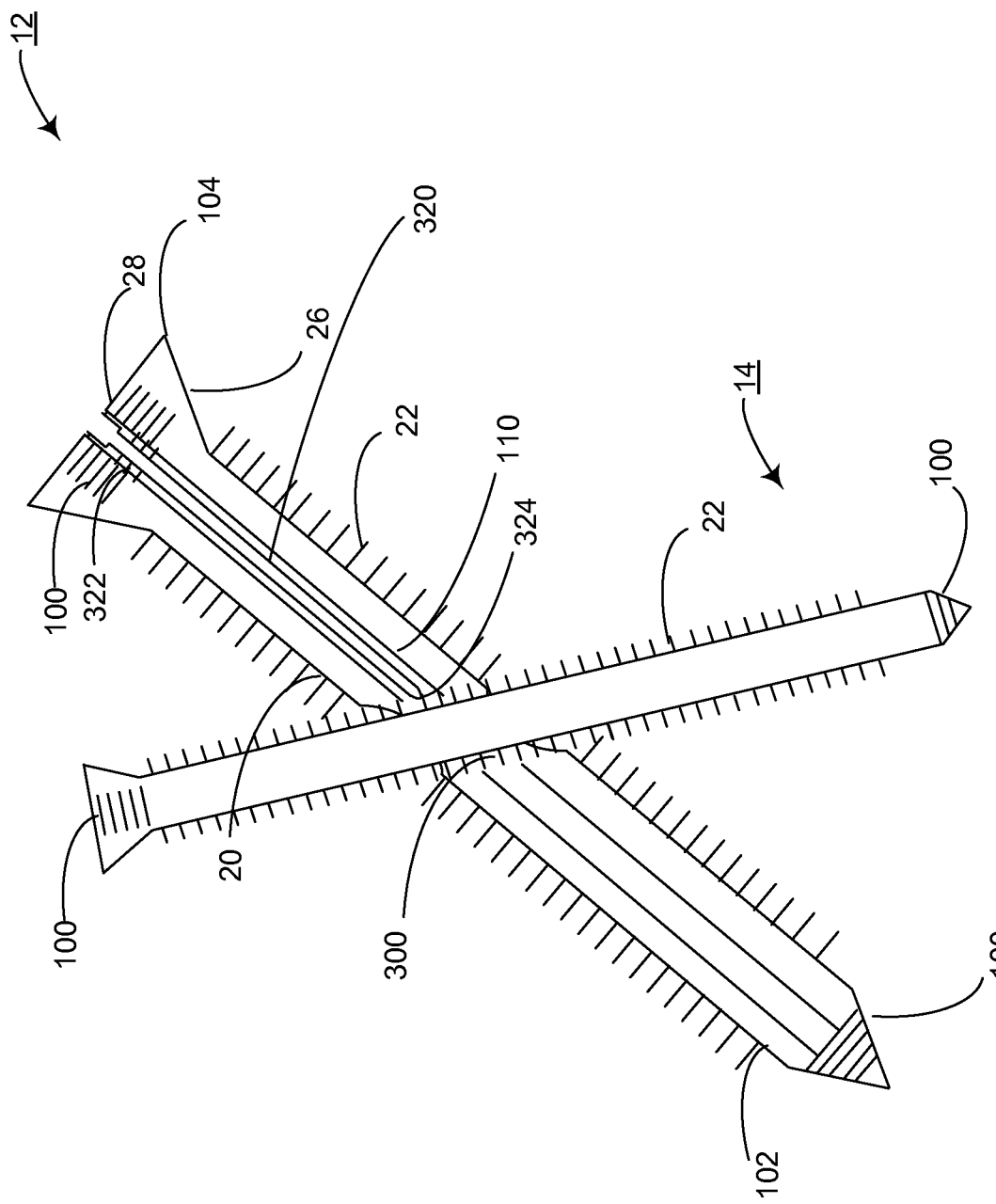
FIG. 19 is a perspective view of the first pedicle screw and an alternative second pedicle screw according to yet another alternative aspect of the present disclosure.

FIG. 19 illustrates yet another aspect of the present disclosure of two pedicle screws, such as the first and second pedicle screws 12 and 14 of the vertebral stabilization assembly 10, in accordance with an embodiment of the present disclosure. In this aspect, the first and second pedicle screws 12 and 14 are coupled as shown in FIG. 18. However, in this aspect, the threaded portion 22 extends along the full length of the second pedicle screw 14, and the second pedicle screw 14 does not contain a non-threaded portion 310.

Referring also to FIG. 20, a top cross-sectional view of a vertebra 118, such as a cervical, lumbar, or thoracic vertebra, is shown with the first pedicle screw 12 and second pedicle screw 14 set therein. One advantage of the vertebral stabilization assembly 10 of the present disclosure is that the first pedicle screw 12 may be secured in a pedicle 120 on an anterior side 124 of the vertebra 118. Another advantage of the present disclosure is that the second pedicle screw 14 may be inserted through the first pedicle screw 12 and locked in place with the locking pin 320. Such an arrangement increases the stability of the screws to prevent them from moving.

Anterior placement to the pedicle 120 of the vertebra 118 provides a surgeon with full access to the disc area. Anterior placement also is capable of distributing compressive loads to the vertebral support members 10 from rotational and translational movement, and preventing displacement of graft material.

As previously mentioned, the connecting member 60 is positionable on the anterior side 124 of the vertebra 118. Thus, the vertebral stabilization assembly 10 of the present disclosure achieves the advantages of anterior vertebral stabilization, since the connecting member 60 is positioned on the anterior side 124 of the vertebra 118.

The first pedicle screw 12 may be placed in the vertebra 118 anteriorly avoiding the disadvantages associated with large, invasive posterior procedures which require significant interference and dissection of adjacent muscles.

In yet another aspect of the present disclosure, the first pedicle screw 12 may comprise the cannulated shaft 20 such that the passageway 110 extends through the shaft 20 from the head 28 to the distal end 102 of the shaft 20. By utilizing the passageway 110 extending through the shaft 20 of the first pedicle screw 12, a tool (not shown) such as a tap or drill bit may be placed through this cannulated portion of the shaft 20 such that the tool or drill bit may enter near the head 28 of the first pedicle screw 12. The tool may then be extended through the passageway 110 towards the distal end 102.

The tool may then be utilized to drill through to a posterior side 122 of the vertebra 118 for location of the distal end 102 of the first pedicle screw 12 from the posterior side 122 of the vertebra 118. Since only a small distance must be drilled, there is minimal risk to damages to other parts of the vertebra 118. Furthermore, once the tool penetrates the posterior side 122 of the vertebra 118, the surgeon should be able to sense the reduced resistance and friction on the tool. Furthermore, the tool may be provided with stops or a drill bit may be cannulated to prevent extension of the drill bit beyond the posterior side 122 of the vertebra 118.

In the present embodiment, right side 128 placement of the first pedicle screw 12 is preferable to avoid injuries to the patient by utilizing a shorter screw with similar construction as of the first pedicle screw 12 to drill into vertebra 118. In some instances, however, left side 126 placement of the first pedicle screw 12 in the vertebra 118 will be necessary. Left side 126 placement of the first pedicle screw 12 was discussed above in greater detail with reference to FIG. 7.

The second pedicle screw 14 may also be placed in the vertebra 118 anteriorly avoiding the disadvantages associated with large, invasive posterior procedures which require significant interference and dissection of adjacent muscles.

In the present embodiment, left side 126 placement of the second pedicle screw 14 is preferable. In some instances, however, right side 128 placement of the first pedicle screw 14 in the vertebra 118 will be necessary.

In yet another aspect of the present disclosure, the second pedicle screw 14 is inserted into the vertebrate 118 through the transverse channel 300 in the first pedicle screw 12. In this configuration, the second pedicle screw 14 is placed in the same plane as the first pedicle screw 12, rather than slightly above or below it. The non-threaded portion 310 of the second pedicle screw 14 will pass through the transverse channel 300 of the first pedicle screw 12. At least a portion of the threaded portion 22 of second pedicle screw 14 may come to rest inside transverse channel 300. The second pedicle screw 14 may be placed through the first pedicle screw 12 at an angle between 0 and 90 degrees. The second pedicle screw 14 may be advantageously secured to the first pedicle screw 12 via the locking pin 320 to prevent movement of the assembly within the vertebrate 118.

FIG. 21 illustrates an alternative top cross-sectional view of the vertebra 118 shown with the first pedicle screw 12 and second pedicle screw 14 set therein. In this view, cross-sections of the first and second pedicle screws 12 and 14 are provided as they would be secured in the final position within the vertebra 118. The locking pin 320 is placed inside the passageway 110 of the first pedicle screw 12.

In one aspect of the present disclosure, the second pedicle screw 14 is placed through the transverse channel 300 within the first pedicle screw 12 to create a vertebral screw arrangement with the locking pin 320, as described in FIG. 19. Once the second pedicle screw 14 is placed, the locking pin 320 may be inserted into the passageway 110 within the first pedicle screw 12. The locking pin 320 may span the entire length of the passageway 110 up to the point of contacting the non-threaded portion 310 or one of the threads of the threaded portion 22 of the second pedicle screw 14. The locking pin 320 may be secured by tightening the threads 312 at the top of the locking pin 320 against the passageway 110 so that the second pedicle screw 14 is rigidly held under tension to the first pedicle screw 12 by the locking pin 320. Such an arrangement advantageously minimizes movement of the screws after they have been placed.

FIG. 22 illustrates yet another alternative aspect of the present disclosure where left side 126 placement of the first pedicle screw 12 is shown. In this view, cross-sections of the first and second pedicle screws 12 and 14 are provided as they would be secured in the final position within the vertebra 118. The locking pin 320 is shown inside passageway 110 of the first pedicle screw 12.

In one aspect of the present disclosure, the second pedicle screw 14 is placed through the transverse channel 300 within the first pedicle screw 12 to create a vertebral screw arrangement with the locking pin 320, as described in FIG. 19. Once the second pedicle screw 14 is placed, the locking pin 320 may be inserted into the passageway 110 within the first pedicle screw 12. The locking pin 320 may span the entire length of the passageway 110 up to the point of contacting the non-threaded portion 310 or one of the threads of the threaded portion 22 of the second pedicle screw 14. The locking pin 320 may be secured by tightening the threads 312 at the top of locking pin 320 against the passageway 110 so that the second pedicle screw 14 is rigidly held under tension to the first pedicle screw 12 by the locking pin 320. Such an arrangement advantageously minimizes movement of the screws after they have been placed.

Thus, it is apparent that there has been provided, in accordance with the present disclosure, a vertebral stabilization assembly and method that satisfies one or more of the advantages set forth above. Although the preferred embodiment has been described in detail, it should be understood that various changes, substitutions, and alterations can be made herein without departing from the scope of the present disclosure, even if all of the advantages identified above are not present. For example, the various embodiments shown in the drawings herein illustrate that the present disclosure may be implemented and embodied in a variety of different ways that still fall within the scope of the present disclosure.

Also, the techniques, designs, elements, and methods described and illustrated in the preferred embodiments as discrete or separate may be combined or integrated with other techniques, designs, elements, or methods without departing from the scope of the present disclosure. Other examples of changes, substitutions, and alterations are readily ascertainable by one skilled in the art and could be made without departing from the spirit and scope of the present disclosure.

The invention claimed is:

1. A vertebral stabilization assembly for stabilizing vertebrae, the assembly comprising:
   a first vertebral screw having a shaft with a first end, a threaded portion, and an engaging portion, the threaded portion configured for threading engagement of the first vertebral screw with a vertebral body of a vertebra; and
   a second vertebral screw having a shaft with a first end, a first threaded portion, a second threaded portion, and an engaging portion, the first and second threaded portions configured for threading engagement of the second vertebral screw with the vertebral body of the vertebra;
   wherein the second vertebral screw is configured to cross through the first vertebral screw while engaged with the vertebral body of the vertebra, wherein the first vertebral screw encloses a passageway, wherein the passageway is configured to enclose a locking pin, wherein the locking in secures the second vertebral screw to the first vertebral screw.

2. The vertebral stabilization assembly of claim 1, wherein the second vertebral screw is secured to the first vertebral screw by the locking pin forcing the second vertebral screw against the first vertebral screw.

3. The vertebral stabilization assembly of claim 1, wherein the locking pin is configured to threadingly engage the passageway.

4. The vertebral stabilization assembly of claim 1, wherein the locking pin engages the first threaded portion of the second vertebral screw.

5. The vertebral stabilization assembly of claim 1, wherein the second vertebral screw further comprises a non-threaded portion between the first threaded portion and the second threaded portion.

6. The vertebral stabilization assembly of claim 1, wherein the first vertebral screw is configured to be placed in a vertebrate using a guide member.

7. The vertebral stabilization assembly of claim 1, wherein the first vertebral screw is inserted into a vertebrate through a patient's right side.

8. The vertebral stabilization assembly of claim 7, wherein the second vertebral screw is inserted into a vertebrate through a patient's left side.

9. The vertebral stabilization assembly of claim 8, wherein the second vertebral screw is secured to the first vertebral screw by the locking pin forcing the second vertebral screw against the first vertebral screw.

10. The vertebral stabilization assembly of claim 9, wherein the locking pin engages a thread of the second vertebral screw.

11. The vertebral stabilization assembly of claim 9, wherein the locking pin threadingly engages the first vertebral screw.

12. The vertebral stabilization assembly of claim 1, wherein the first vertebral screw is inserted into a vertebrate through a patient's left side.

13. The vertebral stabilization assembly of claim 12, wherein the second vertebral screw passes through the first vertebral screw at an angle of less than ninety degrees.

14. The vertebral stabilization assembly of claim 13, wherein the locking pin threadingly engages the first vertebral screw.

15. The vertebral stabilization assembly of claim 12, wherein the second vertebral screw is secured to the first vertebral screw by the locking pin forcing the second vertebral screw against the first vertebral screw.

16. The vertebral stabilization assembly of claim 15, wherein the locking pin engages a thread of the second vertebral screw.

17. The vertebral stabilization assembly of claim 1, wherein the second vertebral screw passes through the first vertebral screw at an angle of less than ninety degrees.

* * * * *